(12) United States Patent
Beveridge et al.

(10) Patent No.: US 10,232,078 B2
(45) Date of Patent: Mar. 19, 2019

(54) CURABLE POLYMERIC MATERIALS AND METHODS OF USING SAME

(71) Applicant: 3M INNOVATIVE PROPERTIES COMPANY, St. Paul, MN (US)

(72) Inventors: Nicole Morozowich Beveridge, Stillwater, MN (US); Cary A. Kipke, Austin, TX (US); James P. DiZio, St. Paul, MN (US); Jerald K. Rasmussen, Woodville, WI (US); George W. Griesgraber, Eagan, MN (US); Andrew P. Klein, St. Paul, MN (US); Athanasios Touris, St. Paul, MN (US); Döne Demirgöz, St. Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 16/061,396

(22) PCT Filed: Dec. 13, 2016

(86) PCT No.: PCT/US2016/066328
§ 371 (c)(1),
(2) Date: Jun. 12, 2018

(87) PCT Pub. No.: WO2017/112456
PCT Pub. Date: Jun. 29, 2017

(65) Prior Publication Data

US 2019/0038799 A1 Feb. 7, 2019

Related U.S. Application Data

(60) Provisional application No. 62/270,824, filed on Dec. 22, 2015.

(51) Int. Cl.
| | | |
|---|---|---|
| *A61L 24/06* | (2006.01) | |
| *A61L 26/00* | (2006.01) | |
| *C08F 220/18* | (2006.01) | |
| *A61K 9/00* | (2006.01) | |
| *B01F 15/00* | (2006.01) | |

(52) U.S. Cl.
CPC .......... *A61L 24/06* (2013.01); *A61L 26/0014* (2013.01); *B01F 15/0087* (2013.01); *C08F 220/18* (2013.01); *B01F 2215/0034* (2013.01)

(58) Field of Classification Search
None
See application file for complete search history.

(56) References Cited

U.S. PATENT DOCUMENTS

| | | |
|---|---|---|
| 4,119,615 A | 10/1978 | Schulze |
| 4,218,351 A | 8/1980 | Rasmussen |
| 4,414,250 A | 11/1983 | Costanza |
| 4,619,979 A | 10/1986 | Kotnour |
| 4,684,710 A | 8/1987 | Schimmel |
| 4,843,134 A | 6/1989 | Kotnour |
| 5,008,137 A | 4/1991 | Nugent, Jr. |
| 5,081,197 A | 1/1992 | Heilmann |
| 5,140,057 A | 8/1992 | Saeki |
| 5,391,633 A | 2/1995 | Saeki |
| 5,637,646 A | 6/1997 | Ellis |
| 5,804,610 A | 9/1998 | Hamer |
| 5,986,011 A | 11/1999 | Ellis |
| 6,635,690 B2 | 10/2003 | Heilmann |
| 6,677,402 B2 | 1/2004 | Gaddam |
| 7,501,184 B2 | 3/2009 | Leir |
| 7,851,574 B2 | 12/2010 | Dollase |
| 8,137,807 B2 | 3/2012 | Clapper |
| 8,729,197 B2 | 5/2014 | Kropp |
| 9,217,050 B2 | 12/2015 | Fornof |
| 2011/0237725 A1 | 9/2011 | Clapper |
| 2012/0142848 A1 | 6/2012 | Bzowej |
| 2012/0289736 A1 | 11/2012 | Yang |
| 2013/0260137 A1 | 10/2013 | Akiyama |
| 2014/0050872 A1 | 2/2014 | Leir |
| 2015/0057428 A1 | 2/2015 | Iyer |

FOREIGN PATENT DOCUMENTS

| | | |
|---|---|---|
| WO | WO 2002/094890 | 11/2002 |
| WO | WO 2002/102909 | 12/2002 |
| WO | WO 2006/024669 | 3/2006 |
| WO | WO 2011/119363 | 9/2011 |
| WO | WO 2012/088126 | 6/2012 |
| WO | WO 2017/112457 | 6/2017 |

OTHER PUBLICATIONS

International Search Report for PCT International Application No. PCT/US2016/066328, dated Mar. 9, 2017, 4 pages.

*Primary Examiner* — Tae H Yoon
(74) *Attorney, Agent, or Firm* — Jean A. Lown

(57) ABSTRACT

Polymeric materials are disclosed herein that include a Polymer A, a Polymer B, and an oxalate ester or reaction product thereof. Polymer A contains electrophilic reactive groups, and Polymer B contains nucleophilic groups. In certain embodiments, the polymeric materials are free-flowing liquids at 100% solids that can be used, for example, as topical skin adhesives.

14 Claims, No Drawings

CURABLE POLYMERIC MATERIALS AND METHODS OF USING SAME

CROSS REFERENCE TO RELATED APPLICATIONS

This application is a national stage filing under 35 U.S.C. 371 of PCT/US2016/066328, filed Dec. 13, 2016, which claims the benefit of U.S. Provisional Application No. 62/270,824, filed Dec. 22, 2015, the disclosure of which is incorporated by reference in its/their entirety herein.

BACKGROUND

The use of topical skin adhesives for medical closures continues to grow. Compared to conventional closure techniques such as sutures and staples, topical skin adhesives offer potential benefits to medical professionals. Exemplary benefits of using topical skin adhesives include a potential reduction in the time required to close an incision or laceration, and less skin trauma, which can result in an improved cosmetic outcome.

Current skin adhesive products are typically cyanoacrylate-based adhesives. Cyanoacrylate-based skin adhesive products generally consist of liquid monomers, do not contain solvent, and require no mixing prior to application. Cyanoacrylate monomers can polymerize in the presence of nucleophiles (e.g., hydroxide ions), and the polymerization is not inhibited by oxygen. The rate of polymerization can vary based on a number of factors including, for example, the moisture content of the environment, and the characteristics of the skin (e.g., nucleophile content of the skin). The polymerization rate can generally be accelerated by exposure of cyanoacrylate-based adhesives to additional nucleophiles such as amines. Although cyanoacrylate-based adhesives can provide materials with high tensile strength and high shear strength, the lack of elasticity and flexibility has practically limited the use of cyanoacrylate-based adhesives to incisions that are not under high tension. The use of cyanoacrylate-based adhesives in surgical procedures has also been limited by variable cure time and high cost.

There is a continuing need for new topical skin adhesives for medical closures.

SUMMARY

Disclosed herein are polymeric materials that can be used as topical skin adhesives. In some embodiments, the polymeric materials disclosed herein may provide a balance between high tensile strength and flexibility, which may allow the polymeric materials disclosed herein to be used in high tension areas for primary closure and/or to provide a protective water-resistant microbial barrier over sutures. In some embodiments, the polymeric materials disclosed herein may also exhibit advantageous properties such as hydrophobicity that may provide a hydrophobic microbial barrier.

In one aspect, the present disclosure provides a polymeric material comprising a reaction product of components comprising: a) Polymer A comprising a plurality of first monomeric units of Formula (I):

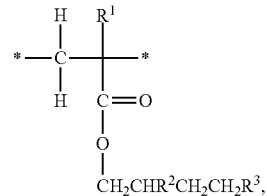

wherein each $R^1$ is independently hydrogen or methyl; each $R^2$ and $R^3$ are independently a linear or branched alkyl having 4 to 14 carbon atoms; and a plurality of second monomeric units of Formula (II), Formula (III), or a mixture thereof:

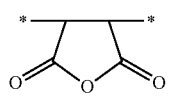

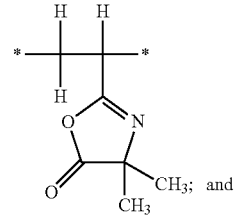

b) Polymer B comprising at least 80 weight percent of a plurality of first monomeric units of Formula (I):

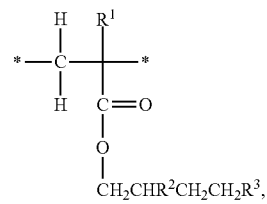

wherein each $R^1$ is independently hydrogen or methyl; each $R^2$ and $R^3$ are independently a linear or branched alkyl having 4 to 14 carbon atoms; and a plurality of monomeric units having a primary amino group; and c) a compound of Formula (IV), a compound of Formula (V), or both:

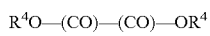

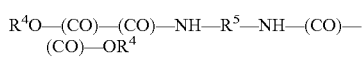

wherein each $R^4$ is independently alkyl, aralkyl, substituted aralkyl, alkenyl, aryl, substituted aryl; and each $R^5$ is independently a divalent hydrocarbon linking group that may optionally include heteroatoms. The present disclosure also provides an adhesive composition comprising the polymeric material described herein.

In another aspect, the present disclosure provides a two-part reactive composition comprising: a) a first part comprising Polymer A and a compound of Formula (IV), a compound of Formula (V), or both, wherein Polymer A comprises: a plurality of first monomeric units of Formula (I):

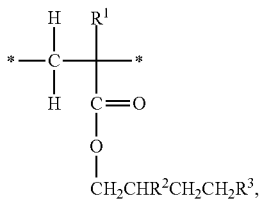

wherein each $R^1$ is independently hydrogen or methyl; each $R^2$ and $R^3$ are independently a linear or branched alkyl having 4 to 14 carbon atoms; and a plurality of second monomeric units of Formula (II), Formula (III), or a mixture thereof:

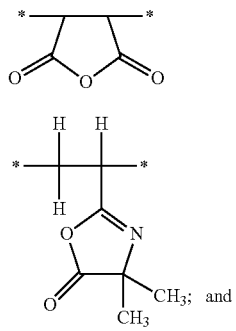

wherein the compounds of Formula (IV) or Formula (V) are of the formulas:

$$R^4O-(CO)-(CO)-OR^4 \quad (IV)$$

$$R^4O-(CO)-(CO)-NH-R^5-NH-(CO)-(CO)-OR^4 \quad (V),$$

wherein: each $R^4$ is independently alkyl, aralkyl, substituted aralkyl, alkenyl, aryl, substituted aryl; and each $R^5$ is independently a divalent hydrocarbon linking group that may optionally include heteroatoms; and b) a second part comprising Polymer B, wherein Polymer B comprises: at least 80 weight percent of a plurality of first monomeric units of Formula (I):

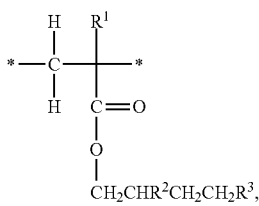

wherein each $R^1$ is independently hydrogen or methyl; independently $R^2$ and $R^3$ are independently a linear or branched alkyl having 4 to 14 carbon atoms; and a plurality of monomeric units having a primary amino group. In some embodiments, the first part is present in a first chamber of a multi-chambered mixing and/or dispensing device, and the second part is present in a second chamber of the multi-chambered mixing and/or dispensing device.

In another aspect, the present disclosure provides a multi-chambered mixing and/or dispensing device containing the two-part reactive composition described herein, wherein the first part is present in a first chamber of the multi-chambered mixing and/or dispensing device, and the second part is present in a second chamber of the multi-chambered mixing and/or dispensing device.

In another aspect, the present disclosure provides a method of preparing a polymeric material comprising: combining the first part and the second part of a two-part reactive composition as described herein under conditions effective for the reaction of the first part and the second part to form the polymeric material.

In another aspect, the present disclosure provides a polymeric material preparable by methods described herein. In some embodiments, the polymeric material is prepared by a method described herein.

As used herein, the term "(meth)acrylic acid" refers to either acrylic acid or methacrylic acid, and the term "(meth)acrylate" refers to either an acrylate group ($H_2C=CH-C(O)-$) or a methacylate group ($H_2C=C(CH_3)-C(O)-$).

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain situations by the term "exactly." As used herein, in connection with a measured quantity, the term "about" refers to that variation in the measured quantity as would be expected by the skilled artisan making the measurement and exercising a level of care commensurate with the objective of the measurement and the precision of the measuring equipment used. Also, as used herein in connection with a measured quantity, the term "approximately" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

When a group is present more than once in a formula described herein, each group is "independently" selected, whether specifically stated or not. For example, when more than one R group is present in a formula, each R group is independently selected. Furthermore, subgroups contained within these groups are also independently selected.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "substituted alkyl" refers to an alkyl substituted with halo, haloalkyl, alkoxy, heteroatoms, or alkoxycarbonyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where R is an alkyl group and (CO) denotes a carbonyl group with the carbon attached to the oxygen with a double bond.

The term "aralkyl" refers to a monovalent group of formula —$R^a$—Ar where R is an alkylene and Ar is an aryl group. That is, the aralkyl is an alkyl substituted with an aryl.

The term "substituted aralkyl" refers to an aralkyl substituted with halo, alkyl, haloalkyl, alkoxy, heteroatoms, or alkoxycarbonyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "substituted aryl" refers to an aryl substituted with halo, alkyl, haloalkyl, alkoxy, heteroatoms, or alkoxycarbonyl.

The term "carbonyl" refers to a divalent group of formula —(CO)— where the carbon atom is attached to the oxygen atom with a double bond.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

As used herein, the term "room temperature" refers to a temperature of 20° C. to 25° C., or more often to a temperature of 21° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Polymeric materials that are free-flowing at 100% solids at room temperature and/or body temperature (e.g., 37° C.) are desirable for use as topical skin adhesives. However, many reactive monomers (e.g., acrylic acid (AA), methacrylic acid (MAA), vinyldimethylazlactone (VDM), N-vinylsuccinimide (NVS), acrylamide (ACM), dimethylaminoethylmethacrylate (DMAEMA), dimethylaminoethylacrylate (DMAEA), N—N-dimethacrylamide (NNDMA), and maleic anhydride (MAH)) used to prepare typical polymeric materials have relatively high Tg values, and often provide copolymers that do not flow at 100% solids at room temperature and/or body temperature.

Polymeric materials that are disclosed herein can be useful, for example, as topical skin adhesives. In some embodiments, the polymeric materials can have relatively high molecular weight and be free-flowing at 100% solids, thus precluding the necessity for solvent. In some embodiments, the viscosities of the polymeric materials can be selected to readily allow for efficient mixing in a two-part adhesive formulation. The polymeric materials can be tailored to impart both hydrophobicity and covalent crosslinking and/or ionic reactivity.

Polymeric materials are disclosed herein that include a Polymer A, a Polymer B, and an oxalate ester. Polymer A contains electrophilic reactive groups, and Polymer B contains nucleophilic groups. The type of reactive groups in the copolymer can determine the extent of both covalent and ionic bond formation. Controlling the ratio of reactive groups in Polymer A and Polymer B can provide the ability to prepare adhesive formulations with a variety of properties (e.g., strength, elasticity, flexibility, hardness, etc.). The relative amounts of electrophilic reactive groups incorporated into Polymer A and Polymer B can influence the resulting adhesive properties obtained after reaction of the components. Specific ratios of the electrophilic and nucleophilic components (mole ratios of the reactive components)

can be tailored to provide a range of adhesive properties, and in particular, adhesive properties suitable for a topical skin adhesive.

Advantageously, in certain embodiments the polymeric materials disclosed herein can provide medical professionals with a reliable, fast curing, skin adhesive having sufficient strength and elasticity for use on surgical incisions. In certain embodiments, the reactive polymeric materials disclosed herein do not require the addition of heat or a catalyst to react; thus, the compositions can typically be reacted at room temperature or body temperature in air (e.g., a nitrogen purge not required). In certain embodiments, a topical skin adhesive that includes the polymeric materials disclosed herein can exhibit adhesive properties during the onset of polymerization (e.g., tackiness), but provide a tack-free hydrophobic barrier after the completion of polymerization.
Polymer A The polymeric compositions disclosed herein include, among other things, at least one Polymer A that contains electrophilic reactive groups and/or a reaction product of Polymer A. In certain embodiments, Polymer A can be prepared with low Tg monomers as those described, for example, in PCT International Publication No. WO 2011/119363 A1 (Clapper et al.) to impart flow characteristics. Particularly useful monomers include those that form monomeric units of Formula (I), as further discussed herein.

Polymer A includes, among other things, a plurality of first monomeric units of Formula (I):

wherein: each $R^1$ is independently hydrogen or methyl; each $R^2$ and $R^3$ are independently a linear or branched alkyl having 4 to 14 carbon atoms. In some embodiments, Polymer A comprises at least 25 weight percent, at least 40 weight percent, at least 60 weight percent, at least 65 weight percent, at least 71 weight percent, or at least 75 weight percent of the monomeric units of Formula (I), based on the total weight of Polymer A. In some embodiments, Polymer A comprises at most 93 weight percent, at most 90 weight percent, at most 80 weight percent, or at most 76 weight percent of the monomeric units of Formula (I), based on the total weight of Polymer A. In some embodiments, Polymer A comprises a range of 25 to 93 weight percent, 40 to 93 weight percent, 60 to 90 weight percent, 65 to 90 weight percent, 71 to 80 weight percent, or 75 to 76 weight percent of the monomeric units of Formula (I), based on the total weight of Polymer A. In other certain embodiments, Polymer A comprises a range of 25 to 80 weight percent, 60 to 90 weight percent, 75 to 93 weight percent, or 71 to 76 weight percent of the monomeric units of Formula (I), based on the total weight of Polymer A. In certain embodiments, Polymer A comprises at least 40 weight percent, at least 60 weight percent, or at least 65 weight percent of the monomeric units of Formula (I), based on the total weight of Polymer A.

The monomeric unit of Formula (I) is a branched alkyl (meth)acrylate. A wide variety of branched alkyl (meth) acrylates can be used for the monomeric unit of Formula (I). Useful branched alkyl (meth)acrylates include (meth)acrylates of 2-alkyl alkanols. Particularly useful branched alkyl (meth)acrylates include, for example, (meth)acrylic acid esters of Guerbet alcohols having 12 to 32 carbon atoms as described in PCT International Publication No. WO 2011/119363 A1 (Clapper et al.).

Polymer A further includes, among other things, a plurality of second monomeric units of Formula (II), Formula (III), or a mixture thereof:

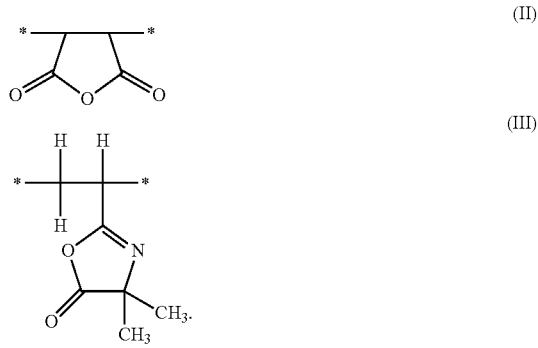

Monomeric units of Formula (II) are maleic anhydride monomeric units (i.e., monomeric units formed from maleic anhydride), and monomeric units of Formula (III) are vinyl dimethyl azlactone monomeric units (i.e., monomeric units formed from vinyl dimethyl azlactone). Monomeric units of Formulas (II) and/or (III) can provide electrophilic reactive groups for Polymer A. Thus nucleophilic groups present in Polymer B, for example, can react with and ring open the maleic anhydride and/or vinyl dimethyl azlactone monomeric units. In some embodiments, Polymer A comprises at least 3 weight percent, at least 6 weight percent, or at least 10 weight percent monomeric units of Formulas (II) and/or (III), based on the total weight of Polymer A. In some embodiments, Polymer A comprises at most 20 weight percent, or at most 15 weight percent monomeric units of Formulas (II) and/or (III), based on the total weight of Polymer A. In some embodiments, Polymer A comprises a range of 3 to 20 weight percent, 6 to 15 weight percent, or 10 to 15 weight percent monomeric units of Formulas (II) and/or (III), based on the total weight of Polymer A.

Optionally, Polymer A can further include, among other things, monomeric units having a siloxane group. A wide variety of monomers having siloxane groups can be used to prepare Polymer A. For one example, (meth)acrylate monomers including one or more siloxane groups (e.g., 3-[tris(trimethylsiloxy)silyl]propyl methacrylate) can be incorporated to provide one or more pendant trimethylsiloxy groups (e.g., tris(trimethylsiloxy)silyl groups). For another example, (meth)acrylate monomers including one or more siloxane chains (e.g., silicone-macromers such as methacryloxy-terminated polydimethylsiloxanes) can be incorporated to provide one or more pendant siloxane chains Typical silicon-macromers can have a weight average molecular weight ($M_w$) of from 5,000 daltons to 100,000 daltons, from 1,000 daltons to 50,000 daltons, from 2,000 daltons to 20,000 daltons, from 5,000 daltons to 15,000 daltons, or about 11,000 daltons. Incorporation of a monomeric unit having a siloxane group into Polymer A may provide benefits such as oxygen permeability, improved feel, and better cosmetic outcomes (e.g., less scarring) when used as a topical skin adhesive.

Optionally, Polymer A can further include, among other things, a monomeric unit comprising an acidic group (i.e., a monomeric unit formed from a monomer comprising an acidic group). Incorporation of a monomeric unit having an acidic group into Polymer A may provide increased hydrogen bonding (e.g., with other acidic groups) and/or increased ionic bonding (e.g., with amino groups) capability, that may result in increased cohesive strength. A wide variety of monomeric units having an acidic group may be incorporated into Polymer A. Useful monomers that can be used to form monomeric units having an acidic group include, for example, acrylic acid, 2-carboxyethyl acrylate, 2-carboxyethyl acrylate oligomers, or a combination thereof. In some embodiments, incorporation of 2-carboxyethyl acrylate and/or 2-carboxyethyl acrylate oligomers may result in more accessible acidic groups for hydrogen and/or ionic bonding, without an increase in Tg that may result from incorporation of acrylic acid.

Optionally, Polymer A can further include, among other things, a monomeric unit comprising a plurality of (meth)acryloyl groups. (Meth)acryloyl groups are of formula $H_2C=CR-(CO)-$ where R is hydrogen or alkyl. In many embodiments, the (meth)acryloyl groups are (meth)arcryloyloxy groups of formula $H_2C=CR-(CO)-O-$. Incorporation of a monomeric unit having a plurality of (meth)acryloyl groups into Polymer A can provide a polymer with similar functionality to that of a linear polymer, but with increased branching. In some embodiments, increased branching may provide increased cohesive strength. A wide variety of monomeric units having a plurality of (meth)acryloyl groups may be incorporated into Polymer A. In some embodiments, the monomeric unit having a plurality of (meth)acryloyl groups has either 3 or 4 (methy)acryloyl groups. Particularly useful monomers that can be used to provide a monomeric unit having a plurality of (meth)acryloyl groups include pentaerythritol tetraacrylate and 1,1,1-trimethylolpropane trimethacrylate. The amount of monomeric units comprising a plurality of (meth)acryloyl groups incorporated into Polymer A can be controlled as desired to provide a balance between cohesive strength and flow properties. In certain embodiments, Polymer A comprises substantially no monomeric units comprising a plurality of (meth)acryloyl groups (e.g., 0 weight percent), based on the total weight of Polymer A. In certain embodiments, Polymer A comprises at most 4 weight percent, or at most 3.5 weight percent of monomeric units comprising a plurality of (meth)acryloyl groups, based on the total weight of Polymer A. In certain embodiments, Polymer A comprises a range of 0 to 4 weight percent, or a range of 0 to 3.5 weight percent of monomeric units comprising a plurality of (meth)acryloyl groups, based on the total weight of Polymer A.

Varying the molecular weight of Polymer A can influence the properties of the resulting polymeric materials. For certain exemplary formulations, to provide flow at 100% solids, a Polymer A with a low molecular weight may be selected. Intrinsic viscosity (IV) is commonly used as a measure of molecular weight of Polymer A. Although a material useful as Polymer A can have a widely varying polydispersity index (PDI), in certain embodiments, the polydispersity index (PDI) can be near 1 such as in a range of 1 to 3, in a range of 1 to 2.5, in a range of 1 to 2, in a range of 1 to 1.5, or in a range of 1 to 1.2.

In certain embodiments, at least one Polymer A has a weight average molecular weight ($M_w$) of at least 10,000 daltons. In certain embodiments, Polymer A has a weight average molecular weight ($M_w$) of no greater than 100,000 daltons. The molecular weight of Polymer A may be controlled by the temperature of the polymerization reaction, concentration of the free radical initiator, addition of a chain transfer agent, and/or concentration of a solvent, as further discussed herein. The molecular weight of Polymer A can be controlled as desired to provide a balance between strength and flow properties.

Optionally, the polymeric material may include two or more species of Polymer A. For example, each species of Polymer A may differ from one another, for example, by composition, molecular weight, branching, and/or quantity and type of electrophilic reactive groups.

In certain embodiments, Polymer A can flow at room temperature and/or body temperature. Polymer A can be considered to flow at room temperature and/or body temperature if it has no fixed shape. In some embodiments, Polymer A can be a viscoelastic fluid at room temperature and/or body temperature.

In some embodiments, Polymer A can have hydrophobic or hydrophilic properties. In certain embodiments, for example, when the polymeric composition is used as a topical skin adhesive, it can be advantageous for Polymer A to have hydrophobic properties to help limit the uptake of aqueous bodily fluids such as blood by the polymeric material.

Polymer B

The polymeric compositions disclosed herein include, among other things, at least one Polymer B that contains nucleophilic groups. In certain embodiments, Polymer B can be prepared with low Tg monomers such as those described, for example, in PCT International Publication No. WO 2011/119363 A1 (Clapper et al.) to impart flow characteristics. Particularly useful monomers include those that can form monomeric units of Formula (I), as further discussed herein.

Polymer B includes, among other things, at least 80 weight percent of a plurality of first monomeric units of Formula (I):

wherein: each $R^1$ is independently hydrogen or methyl; each $R^2$ and $R^3$ are independently a linear or branched alkyl having 4 to 14 carbon atoms. In certain embodiments, Polymer B comprises at least 80 weight percent, at least 90 weight percent, or at least 95 weight percent of a plurality of first monomeric units of Formula (I), based on the total weight of Polymer B. In certain embodiments, Polymer B comprises at most 99.9 weight percent, at most 99.5 weight percent, or at most 99 weight percent of a plurality of first monomeric units of Formula (I), based on the total weight of Polymer B. In certain embodiments, Polymer B comprises a range of 80 to 99.9 weight percent, a range of 90 to 99.5 weight percent, or a range of 95 to 99 weight percent of a plurality of first monomeric units of Formula (I), based on the total weight of Polymer B.

The monomeric unit of Formula (I) is a branched alkyl (meth)acrylate. A wide variety of branched alkyl (meth)acrylates can be used for the monomeric unit of Formula (I).

Useful branched alkyl (meth)acrylates include (meth)acrylates of 2-alkyl alkanols. Particularly useful branched alkyl (meth)acrylates include, for example, (meth)acrylic acid esters of Guerbet alcohols having 12 to 32 carbon atoms as described in PCT International Publication No. WO 2011/119363 A1 (Clapper et al.).

Polymer B further includes, among other things, a plurality of monomeric units having a primary amino group. Monomeric units having a primary amino group provide nucleophilic groups for Polymer B. In certain embodiments, the plurality of monomeric units of Polymer B having the primary amino group is at least three monomeric units.

A wide variety of monomeric units having a primary amino group may be incorporated into Polymer B. In some embodiments, Polymer B comprises at least 0.5 weight percent of monomeric units having a primary amino group, based on the total weight of Polymer B. In some embodiments, Polymer B comprises at most 5 weight percent, at most 4 weight percent, at most 3 weight percent, at most 2 weight percent, or at most 1 weight percent of monomeric units having a primary amino group, based on the total weight of Polymer B. In some embodiments, Polymer B comprises a range of 0.5 to 5 weight percent, 0.5 to 4 weight percent, 0.5 to 3 weight percent, 0.5 to 2 weight percent, or 0.5 to 1 weight percent of monomeric units having a primary amino group, based on the total weight of Polymer B.

Particularly useful monomeric units having a primary amino group include, for example, the reaction product of a diamine with a maleic anhydride monomeric unit (i.e., a monomeric unit formed from maleic anhydride) or a vinyl dimethyl azlactone monomeric unit (i.e., a monomeric unit formed from vinyl dimethyl azlactone).

A wide variety of diamines can be reacted with the monomeric unit formed from maleic anhydride or the monomeric unit formed from vinyl dimethyl azlactone. In certain embodiments, diamines that are C2 or greater are selected to be reacted with the maleic anhydride or vinyl dimethyl azlactone monomeric unit (i.e., a monomeric unit formed from maleic anhydride or vinyl dimethyl azlactone).

In some embodiments, the diamines can include one or more C2-C48 straight chain or cyclic diamines that may optionally include heteroatoms. In certain embodiments, the diamines can include one or more short chain (e.g., C2-C16) diamines, one or more long chain (e.g., C17-C48) diamines, or a mixture of short chain (e.g., C2-C16) and long chain (e.g., C17-C48) diamines. In certain embodiments, the short chain diamines can act as hard segments to impart crystallinity and hydrogen bonding capabilities to the polymeric composition. In certain embodiments, the long chain diamines can impart increased toughness, increased flexibility, and increased hydrophobic character to the polymeric materials.

Useful diamines include, for example, various alkylene diamines such as ethylene diamine, propylene diamine, butanediamine, and hexanediamine; a cyclic diamine such as piperazine; polyether-amines such as polyether diamines available under the trade designation JEFFAMINE RFD-270 available from Huntsman, The Woodlands, Tex.; dimer diamines such as such as those available under the trade designation PRIAMINE from Croda Inc., Edison, N.J.; 3(4),8(9)-bis-(aminomethyl)-tricyclo-[5,2,1,02,6] decane (e.g., available under the trade designation TCD DIAMINE from Oxea, Dallas, Tex.); and combinations thereof. In certain embodiments, a large excess of amine (e.g., 10 equivalents of amine based on the maleic anhydride or vinyl dimethyl azlactone monomeric unit) may be used in the preparation of the monomeric units having the primary amino group.

In some embodiments, monomeric units having a primary amino group can be prepared by polymerizing a monomer having a blocked and/or protected amino group, and removing the blocking or protecting group after the monomer has been polymerized. For example, oximes, carbamates, and tert-Butyloxycarbonyl (BOC) groups, or a combination thereof can be used to block and/or protect the nucleophilic amino groups of, for example, a methacrylate monomer having an amino group (e.g., (2-BOC-amino)ethyl methacrylate).

Optionally, Polymer B can further include, among other things, a monomeric unit comprising a plurality of (meth)acryloyl groups. (Meth)acryloyl groups are of formula $H_2C=CR-(CO)-$ where R is hydrogen or alkyl. In many embodiments, the (meth)acryloyl groups are (meth)arcryloyloxy groups of formula $H_2C=CR-(CO)-O-$. Incorporation of a monomeric unit having a plurality of (meth)acryloyl groups into Polymer B can provide a polymer with similar functionality to that of a linear polymer, but with increased branching. In some embodiments increased branching may provide increased cohesive strength. A wide variety of monomeric units having a plurality of (meth)acryloyl groups may be incorporated into Polymer B. In some embodiments, the monomeric unit having a plurality of (meth)acryloyl groups has either 3 or 4 (methy)acryloyl groups. Particularly useful monomers that can be used to form a monomeric unit having a plurality of (meth)acryloyl groups include pentaerythritol tetraacrylate and 1,1,1-trimethylolpropane trimethacrylate. The amount of monomeric units comprising a plurality of (methy)acryloyl groups incorporated into Polymer B can be controlled as desired to provide a balance between cohesive strength and flow properties. In some embodiments, Polymer B comprises at most 2 weight percent of monomeric units comprising a plurality of (meth)acryloyl groups, based on the total weight of Polymer B. In certain embodiments, Polymer B can have substantially no branching (e.g., 0 percent branching) In certain embodiments, Polymer B can have at most 2 percent branching, at most 1 percent branching, or at most 0.5 percent branching.

Varying the molecular weight of Polymer B can influence the properties of the resulting polymeric materials. For example, a Polymer B with a low molecular weight may be selected for some formulations to provide flow at 100% solids. Intrinsic viscosity (IV) is commonly used as a measure of molecular weight for Polymer B. Although a material useful as Polymer B can have a widely varying polydispersity index (PDI), in certain embodiments, the polydispersity index (PDI) can be near 1 such as in a range of 1 to 3, in a range of 1 to 2.5, in a range of 1 to 2, in a range of 1 to 1.5, or in a range of 1 to 1.2.

In certain embodiments, Polymer B has a weight average molecular weight ($M_w$) of at least 12,000 daltons or at least 18,000 daltons. In certain embodiments, Polymer B has a weight average molecular weight ($M_w$) of at most 100,000 daltons or at most 65,000 daltons. In certain embodiments, Polymer B has a weight average molecular weight ($M_w$) in the range of 12,000 daltons to 100,000 daltons or in the range of 18,000 daltons to 65,000 daltons. The molecular weight of Polymer B may be controlled by the temperature of the polymerization reaction, concentration of the free radical initiator, addition of a chain transfer agent, and/or concentration of a solvent as further discussed herein.

In certain embodiments, Polymer B can flow at room temperature and/or body temperature. Polymer B can be considered to flow at room temperature and/or body temperature if it has no fixed shape. In some embodiments, Polymer B can be a viscoelastic fluid at room temperature and/or body temperature.

In some embodiments, Polymer B can have hydrophobic or hydrophilic properties. In certain embodiments, for example, when the polymeric composition is used as a topical skin adhesive, it can be advantageous for Polymer B to have hydrophobic properties to help limit the uptake of aqueous bodily fluids such as blood by the polymeric material.

Preparation of Polymer A and Polymer B

Polymer A and/or Polymer B can be prepared by free radical polymerization of monomers, such as (meth)acrylate monomers, to form the polymers having the recited monomeric units. In addition to the monomers used to form the various monomeric units described herein, the polymerizable composition used to prepare Polymer A and/or Polymer B typically includes a free radical initiator to commence polymerization of the monomers. The free radical initiator can be a photoinitator or a thermal initiator. The amount of the free radical initiator is often in a range of 0.05 to 5 weight percent based on a total weight of monomers used.

Suitable thermal initiators include various azo compound such as those commercially available under the trade designation VAZO from E. I. DuPont de Nemours Co. (Wilmington, Del., USA), including VAZO 67, which is 2,2'-azobis(2-methylbutane nitrile), VAZO 64, which is 2,2'-azobis(isobutyronitrile), VAZO 52, which is (2,2'-azobis(2,4-dimethylpentanenitrile)), and VAZO 88, which is 1,1'-azobis(cyclohexanecarbonitrile); various peroxides such as benzoyl peroxide, cyclohexane peroxide, lauroyl peroxide, di-tert-amyl peroxide, tert-butyl peroxy benzoate, di-cumyl peroxide, and peroxides commercially available from Atofina Chemicals, Inc. (Philadelphia, Pa.) under the trade designation LUPEROX (e.g., LUPEROX 101, which is 2,5-bis(tert-butylperoxy)-2,5-dimethylhexane, and LUPEROX 130, which is 2,5-dimethyl-2,5-di-(tert-butylperoxy)-3-hexyne); various hydroperoxides such as tert-amyl hydroperoxide and tert-butyl hydroperoxide; and mixtures thereof.

In some embodiments, a photoinitiator may be used. Some exemplary photoinitiators are benzoin ethers (e.g., benzoin methyl ether or benzoin isopropyl ether) or substituted benzoin ethers (e.g., anisoin methyl ether). Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, N.J., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(O-ethoxycarbonyl)oxime. Other suitable photoinitiators include, for example, 1-hydroxycyclohexyl phenyl ketone (commercially available under the trade designation IRGACURE 184), bis(2,4,6-trimethylbenzoyl)phenylphosphineoxide (commercially available under the trade designation IRGACURE 819), 2,4,6-trimethylbenzoylphenylphosphinic acid ethyl ester (commercially available under the trade designation IRGACURE TPO-L), 1-[4-(2-hydroxyethoxy) phenyl]-2-hydroxy-2-methyl-1-propane-1-one (commercially available under the trade designation IRGACURE 2959), 2-benzyl-2-dimethylamino-1-(4-morpholinophenyl) butanone (commercially available under the trade designation IRGACURE 369), 2-methyl-1-[4-(methylthio)phenyl]-2-morpholinopropan-1-one (commercially available under the trade designation IRGACURE 907), and 2-hydroxy-2-methyl-1-phenyl propan-1-one (commercially available under the trade designation DAROCUR 1173 from Ciba Specialty Chemicals Corp. (Tarrytown, N.Y., USA).

The polymerizable composition may optionally further contain a chain transfer agent to control the molecular weight of the resultant (meth)acrylate copolymer. Examples of useful chain transfer agents include, but are not limited to, carbon tetrabromide, alcohols (e.g., ethanol and isopropanol), mercaptans or thiols (e.g., lauryl mercaptan, butyl mercaptan, tert-dodecyl mercaptan, ethanethiol, isooctylthioglycolate, 2-ethylhexyl thioglycolate, 2-ethylhexyl mercaptopropionate, ethyleneglycol bisthioglycolate), and mixtures thereof. If used, the polymerizable mixture may include up to 1 weight percent of a chain transfer agent based on a total weight of monomers. The amount can be up to 0.5 weight percent, up to 0.3 weight percent, up to 0.2 weight percent, or up to 0.1 weight percent and is often equal to at least 0.005 weight percent, at least 0.01 weight percent, at least 0.05 weight percent, or at least 0.1 weight percent. For example, the polymerizable composition can contain 0.005 to 0.5 weight percent, 0.01 to 0.5 weight percent, 0.05 to 0.2 weight percent, 0.01 to 0.2 weight percent, or 0.01 to 0.1 weight percent of a chain transfer agent based on the total weight of monomers.

The polymerizable composition can further include other components such as, for example, antioxidants and/or stabilizers such as hydroquinone monomethyl ether (p-methoxyphenol, MeHQ), and those available under the trade designation IRGANOX 1010 (tetrakis(methylene(3,5-di-tert-butyl-4-hydroxyhydrocinnamate))methane) from BASF Corp. (Florham Park, N.J., USA). The antioxidant and/or stabilizer can be used to increase the temperature stability of the resulting (meth)acrylate copolymer. If used, an antioxidant and/or stabilizer is typically used in the range of 0.01 percent by weight (weight percent) to 1.0 weight percent, based on the total weight of monomers in the polymerizable composition.

The polymerization of the polymerizable composition can occur in the presence or absence of an organic solvent. If an organic solvent is included in the polymerizable composition, the amount is often selected to provide the desired viscosity to the polymerizable composition and to the polymerized composition. Examples of suitable organic solvents include, but are not limited to, methanol, tetrahydrofuran, ethanol, n-propanol, isopropanol, heptane, acetone, methyl ethyl ketone, methyl acetate, ethyl acetate, toluene, xylene, and ethylene glycol alkyl ether. Those solvents can be used alone or combined as mixtures. In some embodiments, the organic solvent is present in an amount 70 weight percent or less, based on the total weight of the polymerizable composition and organic solvent. In some embodiments, the organic solvent is present in an amount 60 weight percent or more, based on the total weight of the polymerizable composition and the organic solvent. If used, any organic solvent typically is removed at the completion of the polymerization reaction or during coating. In some embodiments, the polymerization occurs with little or no organic solvent present. That is the polymerizable composition is free of organic solvent or contains a minimum amount of organic solvent.

Polymer A and/or Polymer B can be prepared by any conventional polymerization method (such as solution polymerization or emulsion polymerization) including thermal bulk polymerization under adiabatic conditions, as is disclosed in U.S. Pat. No. 5,637,646 (Ellis) and 5,986,011 (Ellis et al.). Other methods of preparing Polymer A and/or Polymer B include the continuous free radical polymerization methods described in U.S. Pat. Nos. 4,619,979 and 4,843,134 (Kotnour et al.) and the polymerization within a polymeric package as described in U.S. Pat. No. 5,804,610 (Hamer et al.).

Oxalate Esters and Reaction Products of Oxalate Esters

The polymeric compositions disclosed herein include, among other things, an oxalic acid ester (e.g., an oxalate ester of Formula (IV)), a diamine end-capped with an oxalate ester (e.g., a compound of Formula (V)), or both:

$$R^4O-(CO)-(CO)-OR^4 \quad (IV)$$

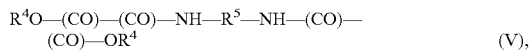

$$R^4O-(CO)-(CO)-NH-R^5-NH-(CO)-(CO)-OR^4 \quad (V)$$

wherein: each $R^4$ is independently alkyl, aralkyl, substituted aralkyl, alkenyl, aryl, substituted aryl; and each $R^5$ is independently a divalent hydrocarbon linking group that may optionally include heteroatoms.

In some embodiments, each $R^4$ is independently an aralkyl substituted with halo, alkyl, haloalkyl, alkoxy, or alkoxycarbonyl. In some embodiments, each $R^4$ is independently an aryl substituted with halo, alkyl, haloalkyl, alkoxy, or alkoxycarbonyl. In certain embodiments, each $R^4$ is methyl, ethyl, n-propyl, i-propyl, n-butyl, t-butyl, or phenyl.

Diamines end-capped with oxalate esters (e.g., of Formula (V)) can be prepared, for example, by reacting a diamine of the formula $H_2N-R^5-NH_2$ with an excess of an oxalate ester of Formula (IV). In certain embodiments, diamines that are C2 or greater are selected to be reacted with the oxalate ester of Formula (IV). Useful diamines include, for example, various alkylene diamines such as ethylene diamine, propylene diamine, butanediamine, and hexanediamine; a cyclic diamine such as piperazine; polyether-amines such as polyether diamines available under the trade designation JEFFAMINE RFD-270 available from Huntsman, The Woodlands, Tex.; dimer diamines such as those available under the trade designation PRI-AMINE from Croda Inc., Edison, N.J.; 3(4),8(9)-bis-(aminomethyl)-tricyclo-[5,2,1,02,6] decane (e.g., available under the trade designation TCD DIAMINE from Oxea, Dallas, Tex.); and combinations thereof. In certain embodiments, compared to equivalents of the amine, an excess based on equivalents of a compound of Formula (IV), as described herein, is reacted with a diamine to prepare a diamine end capped with the oxalate ester. In certain embodiments, compared to equivalents of the diamine, a 10 fold or higher excess, an 8 fold excess, a 6 fold excess, a 5 fold excess, a 4 fold excess, a 3 fold excess, a 2 fold excess, a 1 fold excess, or a 0.5 fold excess of a compound of Formula (IV) as described herein is reacted with the diamine. In some embodiments, excess oxalate ester can be removed from the reaction mixture after the reaction to provide the end-capped diamine. In other embodiments, the mixture of oxalate ester and end-capped diamine can be used directly as a component for the polymeric compositions.

In some embodiments, the use of oxalate esters (e.g., diethyl oxalate) and end-capped diamines can be particularly advantageous for use in the polymeric compositions disclosed herein. For example, although diethyl oxalate is a reactive component, it can also function as a diluent to improve the flow properties of the component materials.

Two Reactive Compositions

In some embodiments, the polymeric materials are prepared as two-part formulations. In some embodiments, the first part includes Polymer A and one or more oxalate esters, and the second part includes Polymer B. In some embodiments, the first part further includes an optional low molecular weight oligomeric or polymeric additive. In some embodiments, the second part further includes an amine additive different than Polymer B. At least in some embodiments, reaction of the first part and the second part can provide both adhesive and cohesive strength, while retaining a sufficient amount of electrophilic reactive groups to react with nucleophilic groups present on human skin.

In certain embodiments, the amounts of Polymer A and Polymer B in the two-part reactive composition are selected such that the molar ratio of the electrophilic reactive groups in Polymer A to the nucleophilic groups in Polymer B is 1:1 or greater, such that electrophilic reactive groups remain after reaction of the components to form the polymeric composition, which can allow for the remaining electrophilic reactive groups to react, for example, with nucleophilic groups present on human skin. In some embodiments, the reaction product is substantially free of amines, some of which can be corrosive to skin.

In certain embodiments, the amounts of Polymer A and Polymer B in the two-part reactive composition are selected such that the molar ratio of the electrophilic reactive groups in Polymer A to the nucleophilic groups in Polymer B is less than 1:1, such that nucleophilic groups remain after reaction of the components to form the polymeric composition, which can allow for the remaining nucleophilic groups to react, for example, with electrophilic reactive groups on the surface of a substrate.

In certain embodiments the molecular weights of Polymer A and Polymer B can be varied as desired to influence the properties of the resulting polymeric materials. For example, if the molecular weight of Polymer A is low, a Polymer B with a higher molecular weight can be selected and while maintaining flow at 100% solids.

In certain embodiments, a ratio of equivalents of the electrophilic reactive groups in the first part to the equivalents of the nucleophilic groups in the second part of the two-part reactive composition can be in a range of 5.8:1 to 0.8 to 1.

Optional Low Molecular Weight Oligomeric or Polymeric Additive for First Part

For embodiments in which Polymer A has a weight average molecular weight ($M_w$) of at least 10,000 daltons, the first part of the two-part reactive composition may optionally include a low molecular weight oligomeric or polymeric additive in addition to Polymer A. In certain embodiments, the oligomeric or polymeric additive contains electrophilic reactive groups. In certain embodiments, the oligomeric or polymeric additive can be prepared with low Tg monomers similar to those disclosed herein for preparing Polymer A.

In certain embodiments, the oligomeric or polymeric additive can be linear or branched. In certain embodiments, the amount of branching can be selected (e.g., a low amount of branching) to provide the desired flow properties for the polymeric composition. In certain embodiments, the oligomeric or polymeric additive has no more than 5 percent branching.

In certain embodiments, the oligomeric or polymeric additive can have a composition similar to that of Polymer A, but with a weight average molecular weight ($M_w$) of less than 10,000 daltons. In some embodiments, the oligomeric or polymeric additive has a weight average molecular weight ($M_w$) of at least 1,000 daltons. In some embodiments, the oligomeric or polymeric additive has a weight average molecular weight ($M_w$) in the range of 1,000 to 7,000 daltons.

In certain embodiments, the oligomeric or polymeric additive can have a composition similar to that of Polymer A, but having a range of 5 to 10 weight percent of monomeric units of Formulas (II) and/or (III), based on the total weight of the oligomeric or polymeric additive.

The oligomeric or polymeric additives can be prepared by methods similar to those described herein for the preparation of, for example, Polymer A.

In certain embodiments, an oligomeric or polymeric additive having a lower molecular weight than Polymer A can advantageously be used to lower the viscosity of the first part of the two-part reactive composition.

Optional Amine Additive for Second Part

In certain embodiments, the second part of the two-part reactive composition may comprise, in addition to Polymer B, an optional diamine additive different than Polymer B.

In some embodiments, the diamine additive can include one or more C2-C48 straight chain or cyclic diamines that may optionally include heteroatoms. In certain embodiments, the diamine additive can include one or more short chain (e.g., C2-C16) diamines, one or more long chain (e.g., C17-C48) diamines, or a mixture of short chain (e.g., C2-C16) and long chain (e.g., C17-C48) diamines. In certain embodiments, the short chain diamines can act as hard segments to impart crystallinity and hydrogen bonding capabilities to the polymeric composition. In certain embodiments, the long chain diamines can impart increased toughness, increased flexibility, and increased hydrophobic character to the polymeric materials.

A wide variety of diamine additives can be added to the second part of the two-part reactive composition. Useful diamines include, for example, various alkylene diamines such as ethylene diamine, propylene diamine, butanediamine, hexanediamine; cyclic diamines such as piperazine; polyether-amines such as polyether diamines available under the trade designation JEFFAMINE RFD-270 available from Huntsman, The Woodlands, Tex.; dimer diamines such as those available under the trade designation PRI-AMINE from Croda Inc., Edison, N.J.; 3(4),8(9)-bis-(aminomethyl)-tricyclo-[5,2,1,02,6] decane (e.g., available under the trade designation TCD DIAMINE from Oxea, Dallas, Tex.); and combinations thereof.

The amount of diamine additive optionally added to the second part of the two-part reactive composition will depend on the amount of electrophilic reactive groups in the first part of the two-part reactive composition and the amount of nucleophilic groups in the second part of the two-part reactive composition, and can be selected to maintain the desired ratio of electrophilic reactive groups to nucleophilic groups.

In certain embodiments, a diamine additive having a relatively low molecular weight compared to the molecular weight of Polymer A and/or Polymer B can advantageously be used to lower the viscosity of the second part of the two-part reactive composition.

Adhesive Compositions

The particular amounts and ratios of electrophilic reactive groups and nucleophilic groups selected will depend on the desired balance properties in the reactive and reacted compositions, and can be readily selected by one of skill in the art in view of the working examples disclosed herein.

Cure time is measured as the amount of time the adhesive can be worked after the adhesive is mixed. After the adhesive is cured, the adhesive can no longer be spread or repositioned. In certain embodiments, the reactive composition can have a cure time at, for example, room temperature or body temperature, in a range of 1 second to 500 seconds, 2 seconds to 250 seconds, 3 seconds to 200 seconds, 5 seconds to 120 seconds, 10 seconds to 90 seconds, or 30 seconds to 75 seconds.

In certain embodiments, the reactive composition can have, before curing, a tack of at least 2, at least 3, at least 4, or at least 5, with tack being measured by qualitative touch and assigned a value from 1 (low tack) to 5 (high tack).

The compositions of the polymeric materials disclosed herein can be varied as desired to achieve useful properties for a reactive composition such as, for example, flow (e.g., to wet a substrate), workability (e.g., for 10 to 90 seconds at room temperature), and tack. In addition, the composition of the polymeric materials disclosed herein can be varied as desired to achieve useful properties after reaction of the polymeric composition such as, for example, cohesive strength, tensile strength, flexibility, and tack.

For example, the curing and cured properties of the polymeric materials will depend on, among other things, the amount of electrophilic reactive groups and nucleophilic groups in the polymeric composition, as well as the ratio of the electrophilic reactive groups (e.g., Polymer A, other low molecular weight oligomeric or polymeric additives, and oxalate esters, typically in the first part of a two-part reactive composition) to nucleophilic groups (e.g., Polymer B and amine additives different than Polymer B, typically in the second part of a two-part reactive composition).

The ratio of the electrophilic reactive groups to nucleophilic groups can be controlled not only by varying the ratio of, for example, Polymer A, Polymer B, and the oxalate ester, but also by varying, for example, the amount of electrophilic reactive groups in Polymer A, and the amount of nucleophilic groups in Polymer B. In addition, more than one Polymer A and/or Polymer B can be used to further vary the amount of reactive groups in the polymeric composition.

Further, additional electrophilic reactive groups can be added to the polymeric materials, for example, by adding optional low molecular weight oligomeric or polymeric materials (e.g., different than Polymer A) to the polymeric composition, typically to the first part of a two-part reactive composition. Similarly, additional nucleophilic groups can be added to the polymeric materials, for example, by adding optional amine additives (e.g., different than Polymer B) to the polymeric composition, typically to the second part of a two-part reactive composition.

In certain embodiments, the molar ratio of the electrophilic reactive groups to the nucleophilic groups in the polymeric composition is selected to be approximately 1:1.

In certain embodiments, the molar ratio of the electrophilic reactive groups to the nucleophilic groups in the polymeric composition is selected to be greater than 1:1, such that electrophilic reactive groups remain after reaction of the components to form the polymeric composition, which can allow for the remaining electrophilic reactive groups to react, for example, with nucleophilic groups present on human skin.

In certain embodiments, the molar ratio of the electrophilic reactive groups to the nucleophilic groups in the polymeric composition is selected to be less than 1:1, such that nucleophilic groups remain after reaction of the components to form the polymeric composition, which can allow for the remaining nucleophilic groups to react, for example, with electrophilic reactive groups on the surface of a substrate.

The compositions of the polymeric materials disclosed herein can also be varied as desired to achieve useful viscosity and flow properties. For example, the molecular weights of Polymer A and Polymer B can independently be varied to achieve useful flow properties. Further, optional low molecular weight oligomeric or polymeric materials different than Polymer A, and optional amine additives different than Polymer B typically can be added to the polymeric compositions to lower viscosity and modify flow properties of the polymeric composition. In addition, the amount of diethyl oxalate, which can function as a diluent to improve the flow properties of the polymeric material, can be varied as desired.

The particular amounts and molecular weights of the various components of the polymeric materials disclosed herein will depend on the desired balance of properties in the reactive and reacted compositions, and can be readily selected by one of skill in the art in view of the working examples disclosed herein.

In certain embodiments, the polymeric materials disclosed herein can be used, for example, as skin or tissue adhesives. Sutures and topical skin adhesives have both been used, either alone or in combination, for wound closure. Topical skin adhesives have been used primarily as tissue sealants in conjunction with sutures, and/or for closure of small wounds. In certain embodiments, the polymeric materials disclosed herein advantageously have properties useful for topical skin adhesives including, for example, one or more of biocompatibility, short cure time, high tensile strength, and flexibility.

Additional materials can be added to the adhesive composition as desired to achieve desirable properties such as mechanical stability, skin adhesion, healing rate, and oxygen permeability. Exemplary additional materials are known in the art and include, but are not limited to, a non-ionic surfactant, a polyethylene glycol, a filler, a dye, an antioxidant, a tackifier, a solvent, a diluent, a viscosity modifier, an antimicrobial agent (e.g., an antibacterial agent), and combinations thereof.

The polymeric materials disclosed herein can be reacted, for example, by providing a two-part reactive composition as described herein; and combining the first part and the second part under conditions effective for the reaction of the first part and the second part to form the polymeric material. In some embodiments the first part and the second part are combined at room temperature. In some embodiments, the first part and the second part are combined at a temperature range of room temperature to 100° C., room temperature to 65° C., or room temperature to 60° C. In some embodiments, the first part and the second part are combined under ambient conditions (e.g., in air without employing a nitrogen purge).

In some embodiments, the first part and the second part of a two-part reactive composition are combined using mixing and/or dispensing methods and/or devices known in the art, such as manual mixing, a mechanical mixing device, an automatic mixing device, a static mixing device, an extrusion mixing device, or a combination thereof. For example, the first part of a two-part reactive composition can be present in a first chamber of a multi-chambered mixing and/or dispensing device (e.g., a first barrel of a dual barreled syringe), and the second part can be present in a second chamber of a multi-chambered mixing and/or dispensing device (e.g., a second barrel of a dual barreled syringe).

Thus, in another aspect, the present disclosure provides a multi-chambered mixing and/or dispensing device containing the two-part reactive composition described herein, wherein the first part is present in a first chamber of the multi-chambered mixing and/or dispensing device, and the second part is present in a second chamber of the multi-chambered mixing and/or dispensing device. In certain embodiments, the multi-chambered mixing and/or dispensing device is a dual barreled syringe containing the two-part reactive composition described herein, wherein the first part is present in a first barrel of the dual barreled syringe, and the second part is present in a second barrel of the dual barreled syringe. Optionally, the dual barreled syringe may include or be connected to a static mixing device to mix the contents of each barrel upon delivery from the syringe.

ILLUSTRATIVE EMBODIMENTS OF THE PRESENT DISCLOSURE

Various embodiments are provided that are polymeric materials, and method of making and using the polymeric materials.

Embodiment 1A is a polymeric material comprising a reaction product of components comprising: a) Polymer A comprising: a plurality of first monomeric units of Formula (I):

wherein: each $R^1$ is independently hydrogen or methyl; each $R^2$ and $R^3$ are independently a linear or branched alkyl having 4 to 14 carbon atoms; and a plurality of second monomeric units of Formula (II), Formula (III), or a mixture thereof:

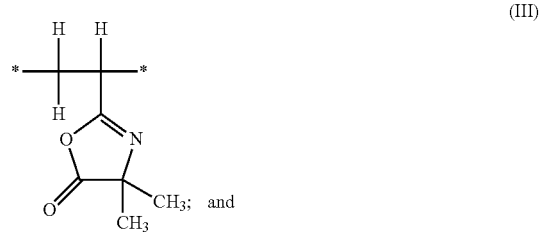

b) Polymer B comprising: a range of 80 to 99.9 weight percent of a plurality of first monomeric units of Formula (I):

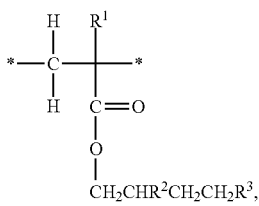

(I)

wherein: each $R^1$ is independently hydrogen or methyl; each $R^2$ and $R^3$ are independently a linear or branched alkyl having 4 to 14 carbon atoms; and a plurality of monomeric units having a primary amino group; and c) a compound of Formula (IV), a compound of Formula (V), or both:

(IV)

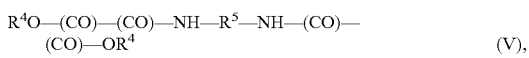

(V), wherein: each $R^4$ is independently alkyl, aralkyl, substituted aralkyl, alkenyl, aryl, or substituted aryl; and each $R^5$ is independently a divalent hydrocarbon linking group that may optionally include heteroatoms.

Embodiment 2A is the polymeric material of embodiment 1A, wherein each $R^4$ is methyl, ethyl, n-propyl, i-propyl, n-butyl, t-butyl, or phenyl.

Embodiment 3A is the polymeric material of embodiment 1A or 2A, wherein Polymer A comprises a range of 25 weight percent to 93 weight percent of the monomeric units of Formula (I).

Embodiment 4A is the polymeric material of any one of embodiments 1A to 3A, wherein Polymer A comprises a range of 40 weight percent to 93 weight percent of the monomeric units of Formula (I).

Embodiment 5A is the polymeric material of any one of embodiments 1A to 4A, wherein Polymer A comprises a range of 60 weight percent to 90 weight percent of the monomeric units of Formula (I).

Embodiment 6A is the polymeric material of any one of embodiments 1A to 5A, wherein Polymer A comprises a range of 65 weight percent to 90 weight percent of the monomeric units of Formula (I).

Embodiment 7A is the polymeric material of any one of embodiments 1A to 6A, wherein Polymer A comprises a range of 71 weight percent to 80 weight percent of the monomeric units of Formula (I).

Embodiment 8A is the polymeric material of any one of embodiments 1A to 7A, wherein Polymer A comprises a range of 75 weight percent to 76 weight percent of the monomeric units of Formula (I).

Embodiment 9A is the polymeric material of any one of embodiments 1A to 8A, wherein Polymer A has a weight average molecular weight ($M_w$) of at least 10,000 daltons.

Embodiment 10A is the polymeric material of any one of embodiments 1A to 9A, wherein Polymer A has a weight average molecular weight ($M_w$) of no greater than 100,000 daltons.

Embodiment 11A is the polymeric material of any one of embodiments 1A to 10A, wherein Polymer A further comprises a monomeric unit comprising a siloxane group.

Embodiment 12A is the polymeric material of embodiment 11A, wherein the siloxane group is a polysiloxane.

Embodiment 13A is the polymeric material of any one of embodiments 1A to 12A, wherein Polymer A further comprises a monomeric unit comprising an acidic group.

Embodiment 14A is the polymeric material of embodiment 13A, wherein the monomeric unit comprising the acidic group is formed from acrylic acid, 2-carboxyethyl acrylate, or 2-carboxyethyl acrylate oligomers.

Embodiment 15A is the polymeric material of any one of embodiments 1A to 14A, wherein Polymer A further comprises a monomeric unit comprising a plurality of (meth) acryloyl groups.

Embodiment 16A is the polymeric material of embodiment 15A, wherein the monomeric unit comprising a plurality of (meth)acryloyl groups is formed from pentaerythritol tetraacrylate or 1,1,1-trimethylolpropane trimethacrylate.

Embodiment 17A is the polymeric material of any one of embodiments 1A to 16A, wherein the plurality of monomeric units of Polymer B having the primary amino group is at least three monomeric units.

Embodiment 18A is the polymeric material of any one of embodiments 1A to 17A, wherein Polymer B comprises a range of 90 to 99.5 weight percent of a plurality of first monomeric units of Formula (I).

Embodiment 19A is the polymeric material of any one of embodiments 1A to 18A, wherein Polymer B comprises a range of 95 to 99 weight percent of a plurality of first monomeric units of Formula (I).

Embodiment 20A is the polymeric material of any one of embodiments 1A to 19A, wherein Polymer B has a weight average molecular weight ($M_w$) in a range of 12,000 daltons to 100,000 daltons.

Embodiment 21A is the polymeric material of any one of embodiments 1A to 20A, wherein Polymer B has a weight average molecular weight ($M_w$) in a range of 18,000 daltons to 65,000 daltons.

Embodiment 22A is the polymeric material of any one of embodiments 1A to 21A, wherein a monomeric unit of the plurality of monomeric units of Polymer B having a primary amino group is a reaction product of a diamine with a monomeric unit formed from maleic anhydride or a monomeric unit formed from vinyl dimethyl azlactone.

Embodiment 23A is the polymeric material of embodiment 22A, wherein the diamine comprises one or more C2-C48 amines.

Embodiment 24A is the polymeric material of embodiment 22A or 23A, wherein the diamine is an alkylene diamine selected from the group consisting of ethylene diamine, propylene diamine, butanediamine, hexanediamine, and combinations thereof.

Embodiment 25A is the polymeric material of embodiment 22A or 23A, wherein the diamine is selected from the group consisting of cyclic diamines, polyether-amines, dimer diamines, 3(4),8(9)-bis-(aminomethyl)-tricyclo-[5,2, 1,02,6] decane, and combinations thereof.

Embodiment 26A is the polymeric material of embodiment 25A, wherein the cyclic diamine is piperazine.

Embodiment 27A is the polymeric material of any one of embodiments 1A to 26A, wherein both Polymer A and Polymer B flow at room temperature.

Embodiment 28A is the polymeric material of any one of embodiments 1A to 27A, wherein both Polymer A and Polymer B are hydrophobic.

Embodiment 29A is the polymeric material of any one of embodiments 1A to 28A, further comprising a component selected from the group consisting of a non-ionic surfactant, a polyethylene glycol, a filler, a dye, an antioxidant, a tackifier, a solvent, a diluent, a viscosity modifier, an antimicrobial agent (e.g., an antibacterial agent), and combinations thereof.

Embodiment 1B is an adhesive composition comprising the polymeric material of any one of embodiments 1A to 29A.

Embodiment 1C is a two-part reactive composition comprising: a) a first part comprising Polymer A and a compound of Formula (IV), a compound of Formula (V), or both, wherein Polymer A comprises: a plurality of first monomeric units of Formula (I):

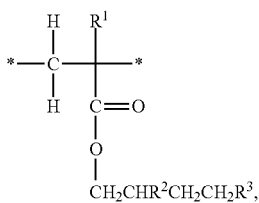

$CH_2CHR^2CH_2CH_2R^3$, (I)

wherein: each $R^1$ is independently hydrogen or methyl; each $R^2$ and $R^3$ are independently a linear or branched alkyl having 4 to 14 carbon atoms; and a plurality of second monomeric units of Formula (II), Formula (III), or a mixture thereof:

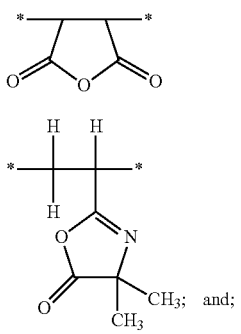

(II)

(III)

wherein the compounds of Formula (IV) or Formula (V) are of the formulas:

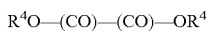

$R^4O$—(CO)—(CO)—$OR^4$ (IV)

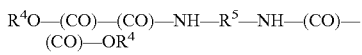

$R^4O$—(CO)—(CO)—NH—$R^5$—NH—(CO)—(CO)—$OR^4$ (V), wherein: each $R^4$ is independently alkyl, aralkyl, substituted aralkyl, alkenyl, aryl, or substituted aryl; and each $R^5$ is independently a divalent hydrocarbon linking group that may optionally include heteroatoms; and b) a second part comprising Polymer B, wherein Polymer B comprises: a range of 80 weight percent to 99.9 weight percent of a plurality of first monomeric units of Formula (I):

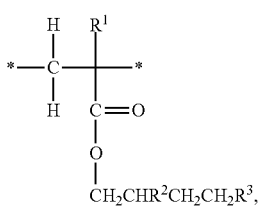

$CH_2CHR^2CH_2CH_2R^3$, (I)

wherein: each $R^1$ is independently hydrogen or methyl; each $R^2$ and $R^3$ are independently a linear or branched alkyl having 4 to 14 carbon atoms; and a plurality of monomeric units having a primary amino group.

Embodiment 2C is the two-part reactive composition of embodiment 1C, wherein each $R^4$ is methyl, ethyl, n-propyl, i-propyl, n-butyl, t-butyl, or phenyl.

Embodiment 3C is the two-part reactive composition of embodiment 1C or 2C, wherein Polymer A comprises a range of 25 weight percent to 93 weight percent of the monomeric units of Formula (I).

Embodiment 4C is the two-part reactive composition of any one of embodiments 1C to 3C, wherein Polymer A comprises a range of 40 weight percent to 93 weight percent of the monomeric units of Formula (I).

Embodiment 5C is the two-part reactive composition of any one of embodiments 1C to 4C, wherein Polymer A comprises a range of 60 weight percent to 90 weight percent of the monomeric units of Formula (I).

Embodiment 6C is the two-part reactive composition of any one of embodiments 1C to 5C, wherein Polymer A comprises a range of 65 weight percent to 90 weight percent of the monomeric units of Formula (I).

Embodiment 7C is the two-part reactive composition of any one of embodiments 1C to 6C, wherein Polymer A comprises a range of 71 weight percent to 80 weight percent of the monomeric units of Formula (I).

Embodiment 8C is the two-part reactive composition of any one of embodiments 1C to 7C, wherein Polymer A comprises a range of 75 weight percent to 76 weight percent of the monomeric units of Formula (I).

Embodiment 9C is the two-part reactive composition of any one of embodiments 1C to 8C, wherein Polymer A further comprises a monomeric unit comprising a siloxane group.

Embodiment 10C is the two-part reactive composition of embodiment 9C, wherein the siloxane group is a polysiloxane.

Embodiment 11C is the two-part reactive composition of any one of embodiments 1C to 10C, wherein Polymer A further comprises a monomeric unit comprising an acidic group.

Embodiment 12C is the two-part reactive composition of embodiment 11C, wherein the monomeric unit comprising the acidic group is formed from acrylic acid, 2-carboxyethyl acrylate, or 2-carboxyethyl acrylate oligomers.

Embodiment 13C is the two-part reactive composition of any one of embodiments 1C to 12C, wherein Polymer A further comprises a monomeric unit comprising a plurality of (meth)acryloyl groups.

Embodiment 14C is the two-part reactive composition of embodiment 13C, wherein the monomeric unit comprising a plurality of (meth)acryloyl groups is formed from pentaerythritol tetraacrylate or 1,1,1-trimethylolpropane trimethacrylate.

Embodiment 15C is the two-part reactive composition of any one of embodiments 1C to 14C, wherein Polymer A has a weight average molecular weight ($M_w$) of no greater than 100,000 daltons.

Embodiment 16C is the two-part reactive composition of any one of embodiments 1C to 15C, wherein Polymer A has a weight average molecular weight ($M_w$) of at least 10,000 daltons.

Embodiment 17C is the two-part reactive composition of embodiment 16C, wherein the first part further comprises an oligomeric or polymeric additive.

Embodiment 18C is the two-part reactive composition of embodiment 17C, wherein the oligomeric or polymeric additive has a weight average molecular weight ($M_w$) of less than 10,000 daltons.

Embodiment 19C is the two-part reactive composition of embodiment 17C or 18C, wherein the oligomeric or polymeric additive comprises: a plurality of first monomeric units of Formula (I):

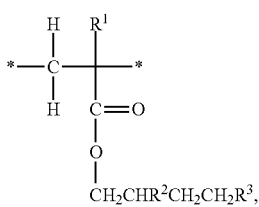

wherein: each $R^1$ is independently hydrogen or methyl; each $R^2$ and $R^3$ are independently a linear or branched alkyl having 4 to 14 carbon atoms; and a plurality of second monomeric units of Formula (II), Formula (III), or a mixture thereof:

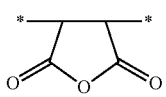

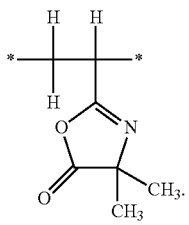

Embodiment 20C is the two-part reactive composition of any one of embodiments 1C to 19C, wherein the plurality of monomeric units of Polymer B having the primary amino group is at least three monomeric units.

Embodiment 21C is the two-part reactive composition of any one of embodiments 1C to 20C, wherein Polymer B comprises a range of 90 to 99.5 weight percent of a plurality of first monomeric units of Formula (I).

Embodiment 22C is the two-part reactive composition of any one of embodiments 1C to 21C, wherein Polymer B comprises a range of 95 to 99 weight percent of a plurality of first monomeric units of Formula (I).

Embodiment 23C is the two-part reactive composition of any one of embodiments 1C to 22C, wherein Polymer B has a weight average molecular weight ($M_w$) in a range of 12,000 daltons to 100,000 daltons.

Embodiment 24C is the two-part reactive composition of any one of embodiments 1C to 23C, wherein Polymer B has a weight average molecular weight ($M_w$) in a range of 18,000 daltons to 65,000 daltons.

Embodiment 25C is the two-part reactive composition of any one of embodiments 1C to 24C, wherein a monomeric unit of the plurality of monomeric units of Polymer B having a primary amino group is a reaction product of a diamine with a monomeric unit formed from maleic anhydride or a monomeric unit formed from vinyl dimethyl azlactone.

Embodiment 26C is the two-part reactive composition of any one of embodiments 1C to 25C, wherein the diamine comprises one or more C2-C48 amines.

Embodiment 27C is the two-part reactive composition of embodiment 25C or 26C, wherein the diamine is an alkylene diamine selected from the group consisting of ethylene diamine, propylene diamine, butanediamine, hexanediamine, and combinations thereof.

Embodiment 28C is the two-part reactive composition of embodiment 25C or 26C, wherein the diamine is selected from the group consisting of cyclic diamines, polyetheramines, dimer diamines, 3(4),8(9)-bis-(aminomethyl)-tricyclo-[5,2,1,02,6] decane, and combinations thereof. Embodiment 29C is the two-part reactive composition of embodiment 28C, wherein the cyclic diamine is piperazine.

Embodiment 30C is the two-part reactive composition of any one of embodiments 1C to 29C, wherein the second part further comprises an amine additive different than Polymer B.

Embodiment 31C is the two-part reactive composition of any one of embodiments 1C to 30C, wherein both Polymer A and Polymer B flow at room temperature.

Embodiment 32C is the two-part reactive composition of any one of embodiments 1C to 31C, wherein both Polymer A and Polymer B are hydrophobic.

Embodiment 33C is the two-part reactive composition of any one of embodiments 1C to 32C, wherein a ratio of equivalents of the electrophilic reactive groups in the first part to the equivalents of the nucleophilic groups in the second part of the two-part reactive composition can be in a range of 5.8:1 to 0.8 to 1.

Embodiment 34C is the two-part reactive composition of any one of embodiments 1C to 33C, further comprising a component selected from the group consisting of a non-ionic surfactant, a polyethylene glycol, a filler, a dye, an antioxidant, a tackifier, a solvent, a diluent, a viscosity modifier, an antimicrobial agent (e.g., an antibacterial agent), and combinations thereof.

Embodiment 35C is the two-part reactive composition of any one of embodiments 1C to 34C, wherein the first part is present in a first chamber of a multi-chambered mixing and/or dispensing device, and the second part is present in a second chamber of a multi-chambered mixing and/or dispensing device.

Embodiment 1D is a multi-chambered mixing and/or dispensing device containing the two-part reactive composition of any one of embodiments 1C to 34C, wherein the first part is present in a first chamber of the multi-chambered mixing and/or dispensing device, and the second part is present in a second chamber of the multi-chambered mixing and/or dispensing device.

Embodiment 1E is a dual barreled syringe containing the two-part reactive composition of any one of embodiments 1C to 34C, wherein the first part is present in a first barrel of a dual barreled syringe, and the second part is present in a second barrel of a dual barreled syringe.

Embodiment 1F is a method of preparing a polymeric material comprising: providing a two-part reactive composition according to any one of embodiments 1C to 35C; and combining the first part and the second part under conditions effective for the reaction of the first part and the second part to form the polymeric material.

Embodiment 2F is the method of embodiment 1F, wherein the conditions effective include combining the first part and the second part at room temperature or body temperature.

Embodiment 3F is the method of embodiment 1F or 2F, wherein combining the first part and the second part comprises mixing the first part and the second part.

Embodiment 4F is the method of any one of embodiments 1F to 3F, wherein the reactive polymeric material has a cure time of 30 seconds to 75 seconds.

Embodiment 1G is a polymeric material preparable by a method according to any one of embodiments 1F to 4F.

Embodiment 1H is a polymeric material prepared by a method according to any one of embodiments 1F to 4F.

Objects and advantages of this disclosure are further illustrated by the following non-limiting examples, but the particular materials and amounts thereof recited in these examples, as well as other conditions and details, should not be construed to unduly limit this disclosure.

EXAMPLES

TABLE 1

List of materials

| Chemical Name/ Abbreviation | Chemical Description | Chemical Source |
|---|---|---|
| C18Acr | C18 acrylate material* | Preparation described below* |
| IOA | Isooctyl acrylate | 3M, St. Paul, MN |
| SiMac | Methacryloxy polydimethyl silicone macromer (Mw 1,000-12,000 Da) | Shin-Etsu Chemical Co., Tokyo, Japan |
| MAH | Maleic anhydride | TCI, Tokyo, Japan |
| VDM | Vinyl dimethyl azlactone | 3M, St. Paul, MN |
| AA | Acrylic acid | Dow Chemical, Midland, MI |
| CEA | 2-Carboxyethyl acrylate | Sigma Aldrich, St. Louis, MO |
| CEAo | 2-Carboxyethyl acrylate oligomers (n = 1-3) | Sigma Aldrich, St. Louis, MO |
| TetAcr | Pentaerythritol tetraacrylate | Polysciences Inc., Warminster, PA |
| TriAcr | 1,1,1-Trimethylolpropane trimethacrylate | Polysciences Inc., Warminster, PA |
| DMAEMA | 2-(Dimethylamino)ethyl methacrylate | 3M, St. Paul, MN |
| ACM | Acrylamide | Mytech-Zibo, China |
| BAPMA | N(-t-BOC-aminopropyl) methacrylamide | Polysciences Inc., Warminster, PA |
| APMA | N-(3-aminopropyl) methacrylamide | Polysciences Inc., Warminster, PA |
| IOTG | Isooctyl thioglycolate | Evans Chemetics LP, Teaneck, NJ |
| VAZO 67 | Trade designation for 2,2'-Asobis(2-methylbutanenitrile) | DuPont, Wilmington, DE |
| THF | Tetrahydrofuran | EMD Chemicals, Gibbstown, NJ |
| $CH_3CN$ | Acetronitrile | EMD Chemicals, Gibbstown, NJ |
| DCM | Dichloromethane | EMD Chemicals, Gibbstown, NJ |
| MEOH | Methanol | EMD Chemicals, Gibbstown, NJ |
| IPA | Isopropyl alcohol | JT Baker, Center Valley, PA |
| EtOAc | Ethyl Acetate | EMD Chemicals, Gibbstown, NJ |
| n-PrOP | n-Propyl alcohol | JT Baker, Center Valley, PA |
| TFA | Trifluoroacetic acid, | VWR, Eagan, MN |
| AMBERLITE | AMBERLITE IR-958, trade designation for Ion Exchange Resin | VWR, Eagan, MN |
| DEO | Diethyl oxylate | TCI Chemicals, Tokyo, Japan |
| PRIAMINE | PRIAMINE 1075; dimer diamine | Croda Inc., Edison, NJ |
| DEO-PRI | Synthesized DEO-P** | Preparation described below |
| 3-TRIS | 3-3-TRIS (trimethylsiloxy) silyl propyl methacrylate | Sigma Aldrich, St. Louis, MO |
| RFD-270 | JEFFAMINE RFD-270 amine is a 270 average formula weight amine containing both rigid (cycloaliphatic) and flexible (polyetheramine) segments in the same molecule | Huntsman, The Woodlands, TX |
| TCD | TCD-diamine: Octahydro-4,7-methano-1H-indenedimethylamine | Oxea, Dallas, TX |
| Prop-diam | 1,3 propane diamine | Alfa Aesar, Ward Hill, MA |

TABLE 1-continued

List of materials

| Chemical Name/ Abbreviation | Chemical Description | Chemical Source |
|---|---|---|
| THF170 | JEFFAMINE THF-170 is a triamine of approximately 1700 molecular weight, based on a PTMEG (poly(tetramethylene ether glycol) | Huntsman, The Woodlands, TX |

*The C18 acrylate material was synthesized by generally following Method 1 of U.S. Pat. No. 8,137,807 and using ISOFOL 18T (available from Sasol) as the starting alkanol. The resulting C18 acrylate material had an approximate distribution of 16% C16, 47% C18 and 32% C20, as determined by Gas Chromatography.
**Synthesis of DEO-PRIAMINE was performed in the following procedure. An amount of 5481.5 grams (37.0 mol) of DEO was added dropwise to a chilled solution of 1000 grams (1.85 mol) of PRIAMINE in 500 mL THF. After all the DEO was added, the solution was warmed to room temperature and mixed for 2 hours. The solution was purified by wiped film evaporation (WFE) and was characterized by 1H NMR.

Equipment

The polymers were prepared by bottle polymerizations using a LAUNDER-OMETER, model number M228AA, available from SDL Atlas of Rock Hill, S.C.

Analytical Testing and Characterization

Nuclear Magnetic Resonance (NMR)

The samples were diluted in deuterated chloroform. The $^1$H NMR spectra were acquired on the samples at room temperature using an Agilent VNMRS 500 FT-NMR spectrometer.

Gel Permeation Chromatography (GPC)

The weight average molecular weight ($M_w$) and the polydispersity index (PDI) for Polymer A and Polymer B preparatory examples were determined using GPC.

Conditions for Samples that Contained Bases:

GPC data were obtained using a Defiant (AGILENT 1100) Size Exclusion Chromatograph with an AGILENT 1260 Refractive Index Detector using two Phenomenex PHENOGEL 10 urn Linear (2) columns with elution times calibrated using polystyrene standards. Approximately 50 mg of solids was dissolved in 10 mL of THF (inhibited with 250 ppm BHT), modified with 2% (v/v) of triethylamine. The resulting solution was run through a 0.45 micron syringe filter and analyzed. All samples were prepared and analyzed in duplicate. The samples were eluted at 1.0 mL/minute.

Conditions for Samples that Contained Acids/No Acid:

GPC data were obtained using an Enterprise (AGILENT 1100) Size Exclusion Chromatograph with an AGILENT 1260 Refractive Index Detector using two Phenomenex PHENOGEL 10 μm Linear (2) columns with elution times calibrated using polystyrene standards. Approximately 50 mg of solids was dissolved in 10 mL of THF (inhibited with 250 ppm BHT). The resulting solution was run through a 0.45 micron syringe filter and analyzed. All samples were prepared and analyzed in duplicate. The samples were eluted at 1.0 mL/minute.

Viscosity

Intrinsic Viscosity (IV):

Samples were tested for IV at various concentration levels, depending on the Mw of the polymer. Concentrations are listed in brackets in g/dL. For below 50K [2.5] was used, for Mw values above 100K [0.8-0.6] was used, and for Mw values above 300K [0.4-0.3] was used. Polymers were dissolved in either EtOAc or THF, depending on the polymer structure. A Lauda PVS Intrinsic Viscosity System and a glass Cannon-Fenske Viscometer were used. The water bath temperature was between 21-24° C.

Inherent Viscosity:

Measurements of copolymers were conducted in glass vials using a Brookfield DV-E Viscometer. A spindle (s64) was inserted into the copolymer composition and operated at speeds ranging from 5 rpm to 50 rpm.

Gas Chromatography (GC)

The analysis was performed using an AGILENT 6890 plus gas chromatograph with a Flame Ionization Detector (FID), an AGILENT 7683A automatic sampler, and an HP-1, 30 meter length, 0.25 mm ID, 1 micrometer $d_f$ film thickness of the stationary phase capillary column. A VDM standard curve was prepared from 1 ppm (W/W) to 100 ppm (W/W) in 50% Acetonitrile (ACN) in Tetrahydrofuran (THF). A PET standard curve was prepared from 1 ppm (W/W) to 100 ppm (W/W) in 50% ACN in THF. A C18Acr standard curve was prepared from 100 ppm (W/W) to 1,000 ppm (W/W) in 50% ACN in THF. The samples were dissolved in THF at 20% (W/W). An aliquot of the dissolved sample was transferred to a vial and weighed. An equal amount of ACN was added to the sample to precipitate the polymer. Finals samples (10%, W/W) were centrifuged and the top layer was used for analysis.

Tensile Loading Test Method

For select adhesive formulations, quantitative tensile measurements were conducted using a modified ASTM 2258-05. The geometry of the test substrate was changed due to sample size and cure time constraints. For all measurements, copolymers (Part A and Part B) were placed in separate compartments using a dual barreled syringe (Sulzer Mixpac AG syringes 1:1 ratio) and the ends were capped with pistons. A plunger was used to move the components to the tip of the dispenser. A mix tip containing a static mixing element was then equipped to the nozzle of the dual barrel syringe. The components were dispensed through a 16-stage static mix tip and measured.

Described below are three versions of the tensile loading test method in which the adhesive formulations were treated/tested under different conditions before measuring.

For all test methods porcine back skin (dermis and epidermis) was harvested and frozen until needed. When needed, porcine skin was thawed at room temperature. The porcine skin was processed by removing the hair with a close shave gentle skin razor. Excess fat and oil was removed using isopropyl alcohol. Samples of porcine skin were then taken using a 12 mm diameter biopsy punch. Test fixtures were made internally consisting of a grip tab to secure to the machine and a 13 mm diameter cylinder to attach to the test substrate. The dermis of the skin sample is adhered to the face of the cylindrical tab using commercially available ethyl cyanoacrylate adhesive. A second biopsy punch of skin is prepared and attached to a text fixture as previously described. Both text fixtures and substrates are then aligned in the grips of a TA-XT2i Texture Analyzer (Texture Technologies Corp./Stable Micro Systems, Hamilton, Mass.) configured for measurement in tension. The gap between the epidermis of the top and bottom skin sample was set to be approximately one half millimeter. Adhesive samples of the Examples were applied between the gaps and allowed to cure for ten minutes. Machine settings used were "Measure Force in Tension" with option "Return to Start" using a 5 kg load cell with crosshead speed of 50 mm/minute. Testing was conducted in a controlled temperature (22.8° C.) and humidity controlled (40% RH) room.

Tensile Loading Test Method Version 1: (Room Temp with No Purging)

Adhesive was stored at room temperature before testing. Samples were repeated in duplicate or triplicate. After adhesive was dispensed from the mix tip, it was directly applied to the porcine skin. Peak force at break was recorded for each sample. "Tack after pull" was measured after the adhesive had broken by bringing the test fixtures back together, allowing the adhesive to sit for one minute, and re-running the test.

Tensile Loading Test Method Version 2: (Room Temp with Tip Purging)

Adhesive was stored at room temperature before testing. Five total test fixtures were aligned as previously described. As the adhesive was pushed out of the mix tip, it was applied to the five test fixtures in quick succession and allowed to cure as previously described. Peak force at break was recorded for only the last three samples and the first two values (purge samples) were discarded. "Tack after pull" was measured after the adhesive had broken by bringing the test fixtures back together, allowing the adhesive to sit for one minute, and re-running the test.

Tensile Loading Test Method Version 3: (Heated with Purging)

The same method as Tensile Loading Test Method Version 2 was performed except the adhesive was warmed to 65° C. and not taken out of the oven until time of application.

Examples EX.1-EX.9

Examples EX.1-EX.9 were prepared by the polymerization reaction of combining two parts: Part A (containing Polymer A) and part B (containing Polymer B). The preparation of various examples of Polymer A and Polymer B are described in more detail below, under the Preparatory Examples section.

The general protocol for the polymerization reaction of copolymer Part A and Part B was followed. Copolymers (Part A and Part B) were placed in separate compartments using a dual barreled syringe (1:1 ratio) and the ends were capped with pistons. The syringe was inverted and a plunger was used to remove air until both components were exiting the nozzle of the dispenser. A mix tip containing a static mixing element was then equipped to the nozzle of the dual barrel syringe. The components were dispensed through the mixing element. All syringe components were obtained from Sulzer Mixpac AG (Switzerland).

Evaluations of cure time, flexibility, and tack were conducted on the adhesive after the components (Part A and Part B) had dispensed from the mix tip.

The cure time was recorded in seconds. Cure time is measured as the amount of time the adhesive can be worked after the adhesive is mixed. After the adhesive is cured, the adhesive can no longer be spread or repositioned.

Flexibility was a qualitative measurement and was assigned a value from 1 (low flexibility, i.e., rigid) to 5 (high flexibility).

Tack was measured by qualitative touch and assigned a value from 1 (low tack) to 5 (high tack).

Tensile loading was also conducted on the final adhesives. Values are reported in g-force. For comparison purposes Dermabond measures 1390.6 with a standard deviation of 587.1.

Examples of Final Adhesive Compositions

Example EX.1

Part A: Preparatory Example 5A (0.9 g) and DEO (0.1 g).
Part B: Preparatory Example 5C (0.4 g), RFD-270 (0.1 g), and PRIAMINE (0.5 g).
Properties: Cure time (11 seconds), initial tack (4), tensile strength (2.5), and flexibility (2.5). Tensile Loading, Version 1: Average peak force. 252.1, standard deviation 103.1. Electrophilic reactive groups: nucleophilic groups equivalent ratio: 1.1.

Example EX.2

Part A: Preparatory Example 13A (0.3 g) and Example 14A (0.6 g), and DEO (0.1 g).
Part B: Preparatory Example 5C (0.55 g), TCD (0.05 g), PRIAMINE (0.4 g).
Properties: Cure time (12 seconds), initial tack (4), tensile strength (2.5), and flexibility (3). Tensile Loading, Version 1: Average peak force. 203.8, standard deviation 80.6. Electrophilic reactive groups: nucleophilic groups equivalent ratio: 1.0.

Example EX.3

Part A: Preparatory Example 3A (0.9 g) and DEO (0.1 g).
Part B: Preparatory Example 6C (0.4 g), TCD (0.1 g), PRIAMINE (0.5 g).
Properties: Cure time (55 seconds), initial tack (3), tensile strength (1), and flexibility (2). Tensile Loading, Version 2: Average peak force. 23.6, standard deviation 16.2. Electrophilic reactive groups: nucleophilic groups equivalent ratio: 1.1.

Example EX.4 (Comparative)

Part A: Preparatory Example 15A (0.6 g) and Preparatory Example 23A (0.4 g).
Part B: Preparatory Example 7C-2 (1.0 g).
Properties: Cure time (555 seconds), initial tack (4), tensile strength (0.5), and flexibility (4). Tensile Loading, Version 3: Average peak force. 79.2, standard deviation 29.3. Electrophilic reactive groups: nucleophilic groups equivalent ratio: 5.8.

Example EX.5

Part A: Preparatory Example 9A (0.3 g) and Preparatory Example 20A (0.35 g), DEO (0.1 g), DEO-PRI (0.25 g).
Part B: Preparatory Example 2C (0.5 g), TCD (0.1 g), and PRIAMINE (0.4 g).
Properties: Cure time (115 seconds), initial tack (3), tensile strength (2), and flexibility (4). Tensile Loading, Version 3: Average peak force. 206.6, standard deviation 68.4. Electrophilic reactive groups: nucleophilic groups equivalent ratio: 1.0.

Example EX.6

Part A: Preparatory Example 15A (0.50 g), Preparatory Example 22A (0.38 g), and DEO (0.12 g).

Part B: Preparatory Example 8C-1 (0.5 g), TCD (0.1 g), and PRIAMINE (0.4 g).
Properties: Cure time (18 seconds), initial tack (2), tensile strength (3), and flexibility (4). Tensile Loading, Version 3: Average peak force. 198.3, standard deviation 63.9. Electrophilic reactive groups: nucleophilic groups equivalent ratio: 0.9.

Example EX.7

Part A: Preparatory Example 15A (0.43 g), Preparatory Example 22A (0.33 g), and DEO-PRI (0.24 g).
Part B: Preparatory Example 8C-2 (0.45 g), Preparatory Example 8C-1 (0.45 g), and TCD (0.1 g).
Properties: Cure time (80 seconds), initial tack (2), tensile strength (3), and flexibility (3). Tensile Loading, Version 3: Average peak force. 189.1, standard deviation 17.6. Electrophilic reactive groups: nucleophilic groups equivalent ratio: 1.1.

Example EX.8

Part A: Preparatory Example 15A (0.31 g), Preparatory Example 21A (0.3 g), DEO (0.1 g), DEO-PRI (0.225 g).
Part B: Preparatory Example 8C-1 (0.5 g), TCD (0.1 g), PRIAMINE (0.4 g).
Properties: Cure time (25 seconds), initial tack (3.75), tensile strength (3.5), flexibility (4). Tensile Loading, Version 3: Average peak force. 788.6, standard deviation 98.1. Electrophilic reactive groups: nucleophilic groups equivalent ratio: 1.0.

Example EX.9

Part A: Preparatory Example 15A (0.31 g), Preparatory Example 22A (0.41 g), DEO (0.1 g), DEO-PRI (0.225 g).
Part B: Preparatory Example 8C-1 (0.4 g), TCD (0.1 g), PRIAMINE (0.4 g).
Properties: Cure time (35 seconds), initial tack (3.5), tensile strength (3), and flexibility (4). Tensile Loading, Version 3: Average peak force. 545.6, standard deviation 390.7. Electrophilic reactive groups: nucleophilic groups equivalent ratio: 1.0.

Preparatory Examples: 1A-23A for Polymer A of Part A

Preparatory Examples 1A-17A were prepared as "Polymer A" (Mw>10 K), a possible component of Part A of the two part adhesive exemplified in EXAMPLES EX.1-EX.9, described above. Preparatory Examples 1A-12A were linear polymers and 13A-17A were branched polymers (branching 0.5-3.5). The approximate percentage amounts of the components of Polymer A in Preparatory Examples 1A-17A were: 45%-90% of C18Acr; 3%-20% of VDM (or another anhydride); 0-50% of SiMac; 0-30% of 3-TRIS; and 0-2% of AA (or another acid).
Preparatory Examples 18A-23A were prepared as "Polymer A," a possible component of Part A of the two part adhesive exemplified in EXAMPLES EX.1-EX.9, described above. Preparatory Examples 18A-19A were linear polymers and 20A-23A were branched polymers (branching 0.5-5).

Preparatory Example 1A: C18Acr-SiMac-VDM-AA
(68.2-20-11.7-0.1)

To a 250 mL amber bottle was added 30.7 grams of C18Acr, 9.0 grams of SiMac, 5.3 grams of VDM, 0.04 grams of AA, 0.405 grams of IOTG, and 0.09 grams of VAZO 67. Ethyl acetate was added to the final composition to provide 30% solids. The components of the bottle were thoroughly degassed using nitrogen, then sealed. The reaction was conducted in a LAUNDER-OMETER at 65° C. for 24 hours. The bottle was removed from the LAUNDER-OMETER and an additional amount of 0.045 grams of VAZO 67 was added under inert conditions. The reaction was continued in the LAUNDER-OMETER at 65° C. for an additional 24 hours. Ethyl acetate was removed from the resulting product using a rotary evaporator. Purification was conducted by precipitation into acetonitrile/acetone 90/10. The copolymer was dried under vacuum at 65° C. and the procedure was repeated two additional times to remove residual impurities. Measured properties were: Mw 18.8K, PDI 2.1, and IV 0.084.

Preparatory Example 2A: C18Acr-SiMac-VDM-AA
(70-18.2-11.7-0.1)

The copolymer was prepared and purified using the same protocol as described in Preparatory Example 1A, with the following exceptions: 31.5 grams of C18Acr, 5.3 grams of VDM, and 8.2 grams of SiMac. The same amounts of 0.04 grams of AA, 0.405 grams of IOTG, and 0.09 grams, plus additional 0.045 grams, of VAZO 67 were used. Measured properties were: Mw 25.8K, PDI 2.1, and IV 0.087.

Preparatory Example 3A: C18Acr-SiMac-VDM-AA
(58.9-32-8.2-1.0)

The copolymer was prepared and purified using the same protocol as described in Preparatory Example 1A, with the following exceptions: 26.5 grams of C18Acr, 3.7 grams of VDM, 14.4 grams of SiMac, and 0.45 grams of AA. The same amount of 0.405 grams of IOTG and 0.090 grams of VAZO 67 were used. Measured properties were: Mw 12.9K, PDI 2.2, and IV 0.079.

Preparatory Example 4A: C18Acr-SiMac-VDM
(45.75-45.75-9)

The copolymer was prepared and purified using the same protocol as described in Preparatory Example 1A, with the following exceptions: 20.5 grams of C18Acr, 4.1 grams of VDM, 20.5 grams of SiMac, 0.36 grams of IOTG, and 0.090 grams of VAZO 67. Measured properties were: Mw 14.3K, PDI 1.6, and IV 0.092.

Preparatory Example 5A: C18Acr-VDM-AA
(88.9-11-0.1)

To a 250 mL amber bottle was added 40.0 grams of C18Acr, 5.0 grams of VDM, 0.04 grams of AA, 0.405 grams of IOTG and 0.09 grams of VAZO 67. Ethyl acetate was added to the final composition to provide 30% solids. The components of the bottle were thoroughly degassed using nitrogen, then sealed. The reaction was conducted in a LAUNDER-OMETER at 65° C. for 24 hours. The bottle was removed from the LAUNDER-OMETER and an additional amount of 0.045 grams of VAZO 67 was added under inert conditions. The reaction was continued in the LAUNDER-OMETER at 65° C. for an additional 24 hours. Ethyl acetate was removed from the resulting product using a rotary evaporator. Purification was conducted by precipitation into acetonitrile. The copolymer was dried under vacuum at 65° C. and the procedure was repeated two additional times to remove residual impurities. Measured properties were: Mw 15.5K, PDI 1.7, and IV 0.064.

Preparatory Example 6A: C18Acr-3-TRIS-VDM (75-5-20)

The copolymer was prepared and purified using the same protocol as described in Preparatory Example 5A, with the following exceptions: 33.8 grams of C18Acr, 9.0 grams of VDM, 2.3 grams of 3-TRIS, 0.210 grams of IOTG, and 0.090 grams of VAZO 67. Measured properties were: Mw 15.5K, PDI 1.7, and IV 0.075.

Preparatory Example 7A: C18Acr-VDM (90-10)

The copolymer was prepared and purified using the same protocol as described in Preparatory Example 5A, with the following exceptions: 40.5 grams of C18Acr, was combined with 4.5 grams of VDM, 0.225 grams of IOTG, and 0.090 grams of VAZO 67. Measured properties were: Mw 12.5K, PDI 1.7, IV 0.062, and Viscosity ~13,500 cPs.

Preparatory Example 8A: C18Acr-VDM-AA (88-11-1)

The copolymer was prepared and purified using the same protocol as described in Preparatory Example 5A, with the following exceptions: 39.6 grams of C18Acr, 5.0 grams of VDM, 0.45 grams of AA, 0.405 grams of IOTG, and 0.090 grams of VAZO 67. Measured properties were: Mw 26.7K, PDI 2.1, and IV 0.101.

Preparatory Example 9A: C18Acr-VDM-AA (79.9-20-0.1)

The copolymer was prepared and purified using the same protocol as described in Preparatory Example 5A, with the following exceptions: 36.0 grams of C18Acr, 9.0 grams of VDM, 0.04 grams of AA, 0.585 grams of IOTG, and 0.090 grams of VAZO 67. Measured properties were: Mw 18.8K, PDI 1.8, and IV 0.075.

Preparatory Example 10A: C18Acr-MAH (90-10)

The copolymer was prepared and purified using the same protocol as described in Preparatory Example 5A, with the following exceptions: 40.5 grams of C18Acr, 4.5 grams of MAH, 0.09 grams of IOTG, and 0.090 grams of VAZO 67. Measured properties were: Mw 18.4K, PDI 1.4, IV 0.066, and Viscosity ~5,500 cPs.

Preparatory Example 11A: C18Acr-MAH (95-5)

The copolymer was prepared and purified using the same protocol as described in Preparatory Example 5A, with the following exceptions: 42.75 grams of C18Acr, 2.25 grams of MAH, 0.15 grams of IOTG, and 0.090 grams of VAZO 67. Measured properties were: Mw 12K, PDI 1.3, IV 0.051, and Viscosity ~3,400 cPs.

Preparatory Example 12A: C18Acr-SiMac-VDM-CEAo (46.3-46.3-6.4-1.1)

The copolymer was prepared and purified using the same protocol as described in Preparatory Example 1A, with the following exceptions: 20.8 grams of C18Acr, 20.8 grams of SiMac, 2.9 grams of VDM, 0.5 grams of CEAo, 0.225 grams of IOTG, and 0.090 grams of VAZO 67. Measured properties were: Mw 31.6K, PDI 1.9, and IV 0.097.

TABLE 2

Summary of Preparatory Examples 1A-12A. (Amounts in grams)

| Prep. Ex # | C18Acr | SiMac | VDM | AA | MAH | CEAo | 3-TRIS | IOTG |
|---|---|---|---|---|---|---|---|---|
| 1A | 30.7 | 9.0 | 5.3 | 0.04 | — | — | — | 0.405 |
| 2A | 31.5 | 8.2 | 5.3 | 0.04 | — | — | — | 0.405 |
| 3A | 26.5 | 14.4 | 3.7 | 0.45 | — | — | — | 0.405 |
| 4A | 20.5 | 20.5 | 4.1 | — | — | — | — | 0.360 |
| 5A | 40.0 | — | 5.0 | 0.04 | — | — | — | 0.405 |
| 6A | 33.8 | — | 9.0 | — | — | — | 2.3 | 0.210 |
| 7A | 40.5 | — | 4.5 | — | — | — | — | 0.225 |
| 8A | 39.6 | — | 5.0 | 0.45 | — | — | — | 0.405 |
| 9A | 36.0 | — | 9.0 | 0.04 | — | — | — | 0.585 |
| 10A | 40.5 | — | — | — | 4.5 | — | — | 0.09 |
| 11A | 42.75 | — | — | — | 2.25 | — | — | 0.15 |
| 12A | 20.8 | 20.8 | 2.9 | — | — | 0.5 | — | 0.225 |

Note:
As described above the amount of VAZO 67 added on day 1 was 0.090 grams and amount of VAZO 67 added on day 2 was 0.045 grams.

Preparatory Example 13A: C18Acr-TriAcr-3-TRIS-VDM (76.5-0.5-8-15)

The copolymer was prepared and purified using the same protocol as described in Preparatory Example 5A, with the following exceptions: 34.4 grams of C18Acr, 6.8 grams of VDM, 3.6 grams of 3-TRIS, 0.25 grams of TriAcr, 0.405 grams of IOTG, and 0.090 grams of VAZO 67. Measured properties were: Mw 12.7K, PDI 1.7, and IV 0.055.

Preparatory Example 14A: C18Acr-TetAcr-VDM (89-1-10)

The copolymer was prepared and purified using the same protocol as described in Preparatory Example 5A, with the following exceptions: 40.1 grams of C18Acr, 4.5 grams of VDM, 0.5 grams of TetAcr, 0.450 grams of IOTG, and 0.090 grams of VAZO 67. Measured properties were: Mw 13.3K, PDI 1.8, and IV 0.051.

Preparatory Example 15A: C18Acr-TetAcr-3-TRIS-VDM (76.5-0.5-8-15)

The copolymer was prepared and purified using the same protocol as described in Preparatory Example 5A, with the following exceptions: 34.4 grams of C18Acr, 6.8 grams of VDM, 3.6 grams of 3-TRIS, 0.25 grams of TetAcr, 0.315 grams of IOTG, and 0.090 grams of VAZO 67. Measured properties were: Mw 15.5K, PDI 1.7, and IV 0.063.

Preparatory Example 16A: C18Acr-VDM-TetAcr (92.5-5-2.5)

The copolymer was prepared and purified using the same protocol as described in Preparatory Example 5A, with the following exceptions: 41.6 grams of C18Acr, 2.3 grams of VDM, 1.13 grams of TetAcr, 0.09 grams of IOTG, and 0.090 grams of VAZO 67. Measured properties were: Mw 28.5K, and IV 0.083.

Preparatory Example 17A: C18Acr-VDM-TetAcr (92.5-5-2.5)

The copolymer was prepared and purified using the same protocol as described in Preparatory Example 5A, with the following exceptions: 41.6 grams of C18Acr, 2.3 grams of VDM, 1.13 grams of TetAcr, 0.225 grams of IOTG, and 0.090 grams of VAZO 67. Measured properties were: Mw 14.4K, and IV 0.057.

TABLE 3

Summary of Preparatory Examples 13A-17A. (Amounts in grams)

| Prep. Ex # | C18Acr | VDM | 3-TRIS | TriAcr | TetAcr | IOTG |
|---|---|---|---|---|---|---|
| 13A | 34.4 | 6.8 | 3.6 | 0.25 | — | 0.405 |
| 14A | 40.1 | 4.5 | — | — | 0.5 | 0.450 |
| 15A | 34.4 | 6.8 | 3.6 | — | 0.25 | 0.315 |
| 16A | 41.6 | 2.3 | — | — | 1.13 | 0.090 |
| 17A | 41.6 | 2.3 | — | — | 1.13 | 0.225 |

Preparatory Example 18A: C18Acr-3-TRIS-VDM (75-5-20)

To a 250 mL amber bottle was added 33.8 grams of C18Acr, 9.0 grams of VDM, 2.3 grams of 3-TRIS, 0.338 grams of IOTG, and 0.090 grams of VAZO 67. Ethyl acetate was added to the final composition to provide 30% solids. The components of the bottle were thoroughly degassed using nitrogen, then sealed. The reaction was conducted in a LAUNDER-OMETER at 65° C. for 24 hours. The bottle was removed from the LAUNDER-OMETER and an additional amount of VAZO 67 (0.045 g) was added under inert conditions. The reaction was continued in the LAUNDER-OMETER at 65° C. for an additional 24 hours. Ethyl acetate was removed from the resulting product using a rotary evaporator. The copolymer was dried at 65° C. under vacuum until confirmed dry by $^1$H NMR. Measured properties were: Mw 11.7K, PDI 1.7, and IV 0.056.

Preparatory Example 19A: C18Acr-VDM (95-5)

The copolymer was prepared and purified using the same protocol as described in Preparatory Example 18A, with the following exceptions: 42.8 grams of C18Acr, 2.3 grams of VDM, 0.225 grams of IOTG, and 0.090 grams of VAZO 67. Measured properties were: Mw 10.8K, PDI 1.6, and IV 0.054.

Preparatory Example 20A: C18Acr-TetAcr-VDM (89-1-10)

The copolymer was prepared and purified using the same protocol as described in Preparatory Example 18A, with the following exceptions: C18Acr (40.1 g), VDM (4.5 g), TetAcr (0.45 g), IOTG (0.475 g) and VAZO 67 (0.090 g). Measured properties were: Mw 11.5K, IV 0.049.

Preparatory Example 21A: C18Acr-TetAcr-VDM (88.5-1.5-10)

The copolymer was prepared and purified using the same protocol as described in Preparatory Example 18A, with the following exceptions: C18Acr (39.8 g), VDM (4.5 g), TetAcr (0.70 g), IOTG (0.450 g) and VAZO 67 (0.090 g). Measured properties were: Mw 8.9K, IV 0.047.

Preparatory Example 22A: C18Acr-TetAcr-VDM (92.5-1.0-6.5)

The copolymer was prepared and purified using the same protocol as described in Preparatory Example 18A, with the following exceptions: C18Acr (41.6 g), VDM (2.9 g), TetAcr (0.45 g), IOTG (0.680 g), VAZO 67 (0.090 g). Measured properties were: Mw 11.7K, IV 0.0515.

Preparatory Example 23A: C18Acr-TetAcr-VDM (92.5-1.0-6.5)

The copolymer was prepared and purified using the same protocol as described in Preparatory Example 18A, with the following exceptions: C18Acr (41.6 g), VDM (2.9 g), TetAcr (0.45 g), IOTG (2.03 g), VAZO 67 (0.090 g). Measured properties were: Mw 5.9K.

TABLE 4

Summary of Preparatory Examples 18A- 23A. (Amounts in grams)

| Prep. Ex # | Linear or Branched | C18Acr | VDM | 3-TRIS | TetAcr | IOTG |
|---|---|---|---|---|---|---|
| 18A | Linear | 33.8 | 9.0 | 2.3 | — | 0.338 |
| 19A | Linear | 42.8 | 2.3 | — | — | 0.225 |
| 20A | Branched | 40.1 | 4.5 | — | 0.45 | 0.475 |
| 21A | Branched | 39.8 | 4.5 | — | 0.70 | 0.450 |
| 22A | Branched | 41.6 | 2.9 | — | 0.45 | 0.680 |
| 23A | Branched | 41.6 | 2.9 | — | 0.45 | 2.03 |

Preparatory Examples: 1B-12B for Polymer B of Part B

Preparatory Examples 1B-12B were prepared as "Polymer B" a possible component of Part B of the two part adhesive exemplified in EXAMPLES EX.1-EX.9, described above. Preparatory Examples 1B-4B 10B were linear un-functionalized polymers with Mw>12K. Preparatory Examples 5B-10B were branched (branching 0.5-2) un-functionalized polymers with Mw>12K. Preparatory Example 11B was a linear un-functionalized polymer with Mw<12K. Preparatory Example 12B was a branched un-functionalized polymer with Mw<12K.

Preparatory Example 1B: C18Acr-VDM (98-2)

To a 250 mL amber bottle was added C18Acr (44.1 g), VDM (0.90 g), IOTG (0.090 g) and VAZO 67 (0.090 g). Ethyl acetate was added to the final composition to provide 30% solids. The components of the bottle were thoroughly degassed using nitrogen, then sealed. The reaction was conducted in a LAUNDER-OMETER at 65° C. for 24 hours. The bottle was removed from the LAUNDER-OMETER and an additional amount of VAZO 67 (0.045 g) was added under inert conditions. The reaction was continued in the LAUNDER-OMETER at 65° C. for an additional 24 hours. Ethyl acetate was removed from the resulting product using a rotary evaporator and the resulting polymer was dissolved in 80 mL THF in preparation for the post-functionalization reaction. Measured properties were: Mw 16.9K, PDI 1.8, and IV 0.066.

Preparatory Example 2B: C18Acr-VDM (98-2)

The copolymer was prepared and purified using the same protocol as described in Preparatory Example 1B, above, with the following exceptions: C18Acr (44.1 g), VDM (0.90 g), and VAZO 67 (0.090 g). Measured properties were: Mw 47.8K, PDI 3.5, and IV 0.111.

Preparatory Example 3B: C18Acr-BAPMA (95-5)

To a 250 ml amber bottle was added C18Acr (42.8 g), BAPMA (1.5 g), IOTG (0.090 g), and VAZO 67 (0.09 g).

Ethyl acetate/n-propanol 90/10 was added to the final composition to provide 45% solids. The components of the bottle were thoroughly degassed using nitrogen, then sealed. The reaction was conducted in a LAUNDER-OMETER at 65° C. for 24 hours. The bottle was removed from the LAUNDER-OMETER and an additional amount of VAZO 67 (0.045 g) was added under inert conditions. The reaction was continued in the LAUNDER-OMETER at 65° C. for an additional 24 hours. Ethyl acetate was removed from the resulting product using a rotary evaporator and the resulting polymer was dissolved in 93.4 ml DCM. Purification of the copolymer was conducted by slowly adding the polymer solution to a rapidly stirred beaker containing a 95/5 ratio of acetone/methanol (500 mL). The clear, colorless copolymer was allowed to settle and the solvent was decanted. The copolymer was dried under vacuum at 65° C. and the procedure was repeated two additional times to remove residual impurities. Measured properties were: Mw 13.8K, PDI 1.8, and IV 0.051.

Preparatory Example 4B: IOA-BAPMA (95-5)

The copolymer was prepared and purified using the same protocol as described in Preparatory Example 3B, with the following exceptions: IOA (42.8 g), BAPMA (1.5 g), IOTG (0.090 g) and VAZO 67 (0.090 g). Measured properties were: Mw 14.1K, PDI 1.9, and IV 0.067.

TABLE 5

Summary of Preparatory Examples 1B-4B. (Amounts in grams)

| Prep. EX # | C18Acr | IOA | VDM | BAPMA | IOTG |
|---|---|---|---|---|---|
| 1B | 44.1 | — | 0.9 | — | 0.090 |
| 2B | 44.1 | — | 0.9 | — | — |
| 3B | 42.8 | — | — | 1.5 | 0.090 |
| 4B | — | 42.8 | — | 1.5 | 0.090 |

Preparatory Example 5B: C18Acr-TetAcr-VDM (97.5-0.5-2)

The copolymer was prepared and purified using the same protocol as described in Preparatory Example 1B, with the following exceptions: C18Acr (43.9 g), VDM (0.90 g), TetAcr (0.23 g) and VAZO 67 (0.090 g). Measured properties were: Mw 37.8K, PDI 4.94, and IV 0.144.

Preparatory Example 6B: C18Acr-TetAcr-VDM (97.5-0.5-2)

The copolymer was prepared and purified using the same protocol as described in Preparatory Example 1B, with the following exceptions: C18Acr (43.9 g), VDM (0.90 g), TetAcr (0.23 g) and VAZO 67 (0.090 g). Measured properties were: Mw 51.6K, PDI 5.3, and IV 0.127.

Preparatory Example 7B: C18Acr-TetAcr-VDM (97.5-0.5-2)

The copolymer was prepared and purified using the same protocol as described in Preparatory Example 1B, with the following exceptions: C18Acr (43.9 g), VDM (0.90 g), TetAcr (0.23 g), IOTG (0.068 g) and VAZO 67 (0.090 g). Measured properties were: Mw 24.9K, PDI 2.2, and IV 0.077.

Preparatory Example 8B: C18Acr-TetAcr-VDM (97.5-0.5-2)

The copolymer was prepared and purified using the same protocol as described in Preparatory Example 1B, with the following exceptions: C18Acr (43.9 g), VDM (0.90 g), TetAcr (0.23 g), IOTG (0.081 g) and VAZO 67 (0.090 g). Measured properties were: Mw 18.5K, PDI 2.0, and IV 0.065.

Preparatory Example 9B: C18Acr-TetAcr-VDM (95.5-0.5-4)

The copolymer was prepared and purified using the same protocol as described in Preparatory Example 1B, with the following exceptions: C18Acr (43.0 g), VDM (1.8 g), TetAcr (0.23 g), IOTG (0.090 g) and VAZO 67 (0.090 g). Measured properties were: Mw 21K, PDI 2.19, and IV 0.071.

Preparatory Example 10B: C18Acr-TetAcr-VDM (95.5-0.5-4)

The copolymer was prepared and purified using the same protocol as described in Preparatory Example 1B, with the following exceptions: C18Acr (43.0 g), VDM (1.8 g), TetAcr (0.23 g), IOTG (0.122 g) and VAZO 67 (0.090 g). Measured properties were: Mw 14.2K, PDI 1.6, and IV 0.057.

TABLE 6

Summary of Preparatory Examples 5B-10B. (Amounts in grams)

| Prep. Ex # | C18Acr | VDM | TetAcr | IOTG |
|---|---|---|---|---|
| 5B | 43.9 | 0.9 | 0.23 | — |
| 6B | 43.9 | 0.9 | 0.23 | — |
| 7B | 43.9 | 0.9 | 0.23 | 0.068 |
| 8B | 43.9 | 0.9 | 0.23 | 0.081 |
| 9B | 43.0 | 1.8 | 0.23 | 0.09 |
| 10B | 43.0 | 1.8 | 0.23 | 0.122 |

Preparatory Example 11B: C18Acr-BAPMA (98-2)

A linear un-functionalized copolymer suitable as Polymer B for Part B was prepared and purified using the same protocol as described in Preparatory Example 3B, with the following exceptions: C18Acr (44.1 g), BAPMA (0.90 g), IOTG (0.090 g) and VAZO 67 (0.090 g). Measured properties were: Mw 9.1K, PDI 1.6, and IV 0.073.

Preparatory Example 12B: C18Acr-TetAcr-VDM (97.5-0.5-2)

The copolymer was prepared and purified using the same protocol as described in Preparatory Example 1B, with the following exceptions: C18Acr (43.9 g), VDM (0.90 g), TetAcr (0.23 g), IOTG (0.225 g) and VAZO 67 (0.090 g). Measured properties were: Mw 10K, PDI 1.6, and IV 0.048.

TABLE 7

Summary of Preparatory Examples 11B-12B. (Amounts in grams)

| Ex # | C18Acr | BAPMA | VDM | TetAcr | IOTG |
|---|---|---|---|---|---|
| 11B | 44.1 | 0.9 | — | — | 0.090 |
| 12B | 44.1 | — | 0.9 | 0.23 | 0.225 |

Preparatory Examples: 1C-12C for Polymer B of Part B

Preparatory Examples 1C-12C were prepared as "Polymer B" a possible component of Part B of the two part adhesive exemplified in EXAMPLES EX.1-EX.9, described above. Preparatory Examples 1C-4C were amine-functionalized polymers with Mw>12K. Preparatory Examples 5C-10C were branched (branching 0.5-2) un-functionalized polymers with Mw>12K. Preparatory Example 11C was a linear amine-functionalized polymer with Mw<12K. Preparatory Example 12C was a branched amine-functionalized polymer with Mw<12K.

Preparatory Example 1C: C18Acr-Prop-Diam-VDM Adduct (98-2)

C18Acr/VDM copolymer from Preparatory example 1B (40 g, $5.75 \times 10^{-3}$ mol VDM) was dissolved in 80 ml THF. The copolymer was added dropwise at room temperature into a stirred solution of 1, 3-propanediamine (4.26 g, $5.75 \times 10^{-2}$ mol) in 10 ml THF. After 10 minutes, the solution was heated to 80° C. under vacuum to remove solvent. The excess diamine was removed by precipitation into acetonitrile. Purification of the copolymer was conducted by slowly adding the polymer solution to a rapidly stirred beaker containing acetonitrile (500 mL). The clear, colorless copolymer was allowed to settle and the solvent was decanted. The copolymer was dried under vacuum at 65° C. and the procedure was repeated two additional times to remove residual impurities.

Preparatory Example 2C: C18Acr-Prop-Diam-VDM Adduct (98-2)

Preparatory Example 2C was prepared in the same manner as Preparatory Example 1C except that copolymer 2B was used as the starting material instead of copolymer 1B.

Preparatory Example 3C: C18Acr-BAPMA (95-5)

C18Acr-BAPMA copolymer (40 g, $3.6 \times 10^{-2}$ mol BAPMA) from Preparatory Example 2B was dissolved in 93.4 ml DCM to make a 30% solution. To this was added TFA (20.64 mL, $1.6 \times 10^{-1}$ mol acid). This mixture was stirred for 2-4 hours at reflux. Upon cooling the solution was filtered through an ion exchange resin (Amberlite IRA-958 (C1)) until the solution was neutralized. DCM was removed from the resulting product using a rotary evaporator. The polymer was dried under vacuum and analyzed by $^1$H NMR. Full deprotection was evident by the disappearance of the BOC-protecting group at 1.43 ppm.

Preparatory Example 4C: IOA-APMA (95-5)

The copolymer was prepared and purified using the same protocol as described in Preparatory Example 3C, except that IOA (44.1 g) was used instead of C18Acr in the analogous 2B Preparatory Example used as the starting material.

Preparatory Example 5C: C18Acr-TetAcr-Prop-Diam-VDM Adduct (97.5-0.5-2)

The copolymer was prepared and purified using the same protocol as described in Preparatory Example 1C, with the following exceptions: Copolymer 5B (40 g, $5.75 \times 10^{-3}$ mol VDM) and 1,3-propanediamine (4.26 g, $5.75 \times 10^{-2}$ mol).

Preparatory Example 6C: C18Acr-TetAcr-Prop-Diam-VDM Adduct (97.5-0.5-2)

The copolymer was prepared and purified using the same protocol as described in Preparatory Example 1C, with the following exceptions: Copolymer 6B (40 g, $5.75 \times 10^{-3}$ mol VDM) and 1, 3-propanediamine (4.26 g, $5.75 \times 10^{-2}$ mol).

Preparatory Example 7C-1: C18Acr-TetAcr-TCD-VDM Adduct (97.5-0.5-2)

The copolymer was prepared and purified using the same protocol as described in Preparatory Example 1C, with the following exceptions: Copolymer 7B (40 g, $5.75 \times 10^{-3}$ mol VDM) and TCD (11.17 g, $5.75 \times 10^{-2}$ mol).

Preparatory Example 7C-2: C18Acr-TetAcr-RFD270-VDM Adduct (97.5-0.5-2)

The copolymer was prepared and purified using the same protocol as described in Preparatory Example 1C, with the following exceptions: Copolymer 7B (40 g, $5.75 \times 10^{-3}$ mol VDM) and RFD-270 (15.52 g, $5.75 \times 10^{-2}$ mol).

Preparatory Example 7C-3: C18Acr-TetAcr-THF170-VDM Adduct (97.5-0.5-2)

The copolymer was prepared and purified using the same protocol as described in Preparatory Example 1C, with the following exceptions: Copolymer 7B (40 g, $5.75 \times 10^{-3}$ mol VDM) and THF170 (67.24 g, $5.75 \times 10^{-2}$ mol).

Preparatory Example 8C-1: C18Acr-TetAcr-TCD-VDM Adduct (97.5-0.5-2)

The copolymer was prepared and purified using the same protocol as described in Preparatory Example 1C, with the following exceptions: Copolymer 8B (40 g, $5.75 \times 10^{-3}$ mol VDM) and TCD (11.17 g, $5.75 \times 10^{-2}$ mol).

Preparatory Example 8C-2: C18Acr-TetAcr-PRIAMINE-VDM Adduct (97.5-0.5-2)

The copolymer was prepared and purified using the same protocol as described in Preparatory Example 1C, with the following exceptions: Copolymer 8B (40 g, $5.75 \times 10^{-3}$ mol VDM) and PRIAMINE (31.03 g, $5.75 \times 10^{-2}$ mol).

Preparatory Example 9C: C18Acr-TetAcr-Prop-Diam-VDM Adduct (95.5-0.5-4)

The copolymer was prepared and purified using the same protocol as described in Preparatory Example 1C, with the following exceptions: Copolymer 9B (40 g, $1.25 \times 10^{-2}$ mol VDM) and 1,3-propanediamine (8.52 g, $1.25 \times 10^{-1}$ mol).

Preparatory Example 10C:
C18Acr-TetAcr-Prop-Diam-VDM-Adduct
(95.5-0.5-4)

The copolymer was prepared and purified using the same protocol as described in Preparatory Example 1C, with the following exceptions: Copolymer 10B (40 g, $1.25 \times 10^{-2}$ mol VDM) and 1,3-propanediamine (8.52 g, $1.25 \times 10^{-1}$ mol).

Preparatory Example 11C: C18Acr-BAPMA (98-2)

The linear amine-functionalized copolymer was prepared and purified using the same protocol as described in Preparatory Example 3C with the following exceptions: Copolymer 11B (40 g, $1.44 \times 10^{-3}$ mol BAPMA) and TFA (8.26 mL, $6.4 \times 10^{-2}$ mol acid).

Preparatory Example 12C:
C18Acr-TetAcr-Prop-Diam-VDM Adduct
(97.5-0.5-2)

The branched amine-functionalized copolymer was prepared and purified using the same protocol as described in Preparatory Example 1C, with the following exceptions: Copolymer 12B (40 g, $5.75 \text{ e}^{-3}$ mol VDM) and 1,3-propanediamine (4.26 g, $5.75 \times 10^{-2}$ mol).

All cited references, patents, or patent applications in the above application are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:
1. A two-part reactive composition comprising:
a) a first part comprising Polymer A and a compound of Formula (IV), a compound of Formula (V), or both, wherein Polymer A comprises:
   a plurality of first monomeric units of Formula (I):

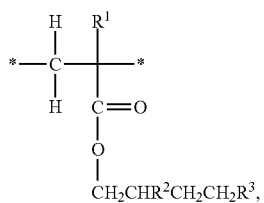

wherein:
   each $R^1$ is independently hydrogen or methyl;
   each $R^2$ and $R^3$ are independently a linear or branched alkyl having 4 to 14 carbon atoms; and
a plurality of second monomeric units of Formula (II), Formula (III), or a mixture thereof:

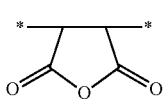

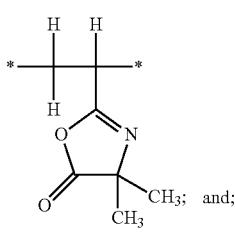

wherein the compounds of Formula (IV) or Formula (V) are of the formulas:

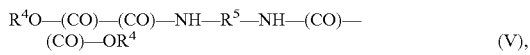

wherein:
   each $R^4$ is independently alkyl, aralkyl, substituted aralkyl, alkenyl, aryl, substituted aryl; and
   each $R^5$ is independently a divalent hydrocarbon linking group that may optionally include heteroatoms; and
b) a second part comprising Polymer B, wherein Polymer B comprises:
at least 80 weight percent of a plurality of first monomeric units of Formula (I):

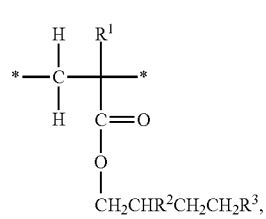

wherein:
   each $R^1$ is independently hydrogen or methyl;
   independently $R^2$ and $R^3$ are independently a linear or branched alkyl having 4 to 14 carbon atoms; and
   a plurality of monomeric units having a primary amino group.

2. The two-part reactive composition of claim 1, wherein Polymer A comprises a range of 25 to 93 weight percent of the monomeric units of Formula (I).

3. The two-part reactive composition of claim 1, wherein Polymer A further comprises a monomeric unit comprising a siloxane group.

4. The two-part reactive composition of claim 1, wherein Polymer A further comprises a monomeric unit formed from a monomer comprising an acidic group selected from the group consisting of acrylic acid, 2-carboxyethyl acrylate, 2-carboxyethyl acrylate oligomers, and combinations thereof.

5. The two-part reactive composition of claim 1, wherein Polymer A further comprises a monomeric unit comprising a plurality of (meth)acryloyl groups.

6. The two-part reactive composition of claim 1, wherein Polymer A has a weight average molecular weight ($M_w$) in a range of 10,000 Daltons to 100,000 Daltons.

7. The two-part reactive composition of claim 6, wherein the first part further comprises an oligomeric or polymeric additive having a weight average molecular weight (Mw) of less than 10,000 Daltons.

8. The two-part reactive composition of claim 7, wherein the oligomeric or polymeric additive comprises:

a plurality of first monomeric units of Formula (I):

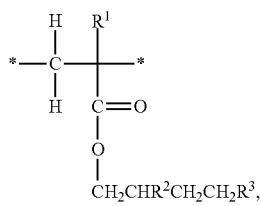

(I)

wherein:
each $R^1$ is independently hydrogen or methyl;
each $R^2$ and $R^3$ are independently a linear or branched alkyl having 4 to 14 carbon atoms; and a plurality of second monomeric units of Formula (II), Formula (III), or a mixture thereof:

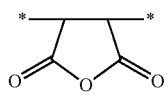

(II)

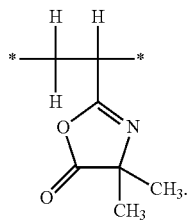

(III)

9. The two-part reactive composition of claim 1, wherein Polymer B has a weight average molecular weight ($M_w$) of at least 12,000 Daltons and a weight average molecular weight ($M_w$) of no greater than 100,000 Daltons.

10. The two-part reactive composition of claim 1, wherein a monomeric unit of the plurality of monomeric units of Polymer B having a primary amino group is a reaction product of a diamine with a monomeric unit formed from maleic anhydride or a monomeric unit formed from vinyl dimethyl azlactone.

11. The two-part reactive composition of claim 1, wherein the second part further comprises an amine additive different than Polymer B.

12. A multi-chambered mixing and/or dispensing device containing the two-part reactive composition of claim 1, wherein the first part is present in a first chamber of the multi-chambered mixing and/or dispensing device, and the second part is present in a second chamber of the multi-chambered mixing and/or dispensing device.

13. A method of preparing a polymeric material comprising:
providing a two-part reactive composition according to claim 1; and
combining the first part and the second part under conditions effective for the reaction of the first part and the second part to form the polymeric material.

14. The method of claim 13, wherein conditions effective for the reaction of the first part and the second part to form the polymeric material comprise room temperature or body temperature.

* * * * *

UNITED STATES PATENT AND TRADEMARK OFFICE
CERTIFICATE OF CORRECTION

PATENT NO. : 10,232,078 B2
APPLICATION NO. : 16/061396
DATED : March 19, 2019
INVENTOR(S) : Nicole Beveridge It is certified that error appears in the above-identified patent and that said Letters Patent is hereby corrected as shown below:

In the Specification

Column 4,
Line 24, delete "methacylate" and insert -- methacrylate --, therefor.

Column 5,
Line 57, Delete "R" and insert -- $R^a$ --, therefor.

Column 8,
Line 58, after "chains" insert -- . --.

Column 9,
Line 23, delete "(meth)arcryloyloxy" and insert -- (meth)acryloyloxy --, therefor.

Column 12,
Line 19, delete "(meth)arcryloyloxy" and insert -- (meth)acryloyloxy --, therefor.
Line 41, after "branching)" insert -- . --.

Column 13,
Line 23, delete "photoinitator" and insert -- photoinitiator --, therefor.

Column 15,
Line 3, delete "No." and insert -- Nos. --, therefor.

Column 16,
Line 1, delete "Two" and insert -- Two-Part --, therefor.

Column 20,
Line 41, delete "R'" and insert -- $R^1$ --, therefor.

Signed and Sealed this
Third Day of September, 2019

Andrei Iancu
*Director of the United States Patent and Trademark Office*

Column 28,
Line 16, delete "(Mw" and insert -- ($M_w$ --, therefor.
Line 38, delete "Asobis(" and insert -- Azobis( --, therefor.
Line 42, delete "Acetronitrile" and insert -- Acetonitrile --, therefor.
Line 57, delete "oxylate" and insert -- oxalate --, therefor.

Column 29,
Line 35, delete "urn" and insert -- μm --, therefor.

Column 38,
Line 32, delete "10B".